(12) United States Patent
Park et al.

(10) Patent No.: US 11,223,017 B2
(45) Date of Patent: Jan. 11, 2022

(54) ORGANIC LIGHT EMITTING DEVICE

(71) Applicant: LG CHEM, LTD., Seoul (KR)

(72) Inventors: Tae Yoon Park, Daejeon (KR); Sang Young Jeon, Daejeon (KR); Min Seung Chun, Daejeon (KR); Seong Mi Cho, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 644 days.

(21) Appl. No.: 15/744,508

(22) PCT Filed: Jun. 26, 2017

(86) PCT No.: PCT/KR2017/006722
§ 371 (c)(1),
(2) Date: Jan. 12, 2018

(87) PCT Pub. No.: WO2018/048074
PCT Pub. Date: Mar. 15, 2018

(65) Prior Publication Data
US 2019/0006590 A1    Jan. 3, 2019

(30) Foreign Application Priority Data

Sep. 6, 2016 (KR) .................. 10-2016-0114284

(51) Int. Cl.
| | | |
|---|---|---|
| *H01L 51/54* | (2006.01) |
| *H01L 51/00* | (2006.01) |
| *C07D 307/91* | (2006.01) |
| *C09K 11/06* | (2006.01) |
| *H01L 51/50* | (2006.01) |
| *C07C 211/54* | (2006.01) |
| *C07D 403/04* | (2006.01) |
| *C07D 251/24* | (2006.01) |
| *C07D 209/82* | (2006.01) |
| *C07C 211/61* | (2006.01) |
| *C07D 209/86* | (2006.01) |
| *C07D 403/10* | (2006.01) |
| *C07D 405/14* | (2006.01) |

(52) U.S. Cl.
CPC .......... *H01L 51/006* (2013.01); *C07C 211/54* (2013.01); *C07C 211/61* (2013.01); *C07D 209/82* (2013.01); *C07D 209/86* (2013.01); *C07D 251/24* (2013.01); *C07D 307/91* (2013.01); *C07D 403/04* (2013.01); *C07D 403/10* (2013.01); *C07D 405/14* (2013.01); *C09K 11/06* (2013.01); *H01L 51/00* (2013.01); *H01L 51/0052* (2013.01); *H01L 51/0058* (2013.01); *H01L 51/0061* (2013.01); *H01L 51/0067* (2013.01); *H01L 51/0072* (2013.01); *H01L 51/0073* (2013.01); *H01L 51/0085* (2013.01); *H01L 51/50* (2013.01); *H01L 51/504* (2013.01); *H01L 51/5008* (2013.01); *C07C 2603/18* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *C09K 2211/1029* (2013.01); *C09K 2211/1033* (2013.01); *C09K 2211/185* (2013.01); *H01L 51/0056* (2013.01); *H01L 51/5016* (2013.01); *H01L 51/5056* (2013.01); *H01L 51/5072* (2013.01); *H01L 2251/5384* (2013.01)

(58) Field of Classification Search
CPC .......... H01L 2251/5384; H01L 51/504; H01L 51/006; H01L 51/00; H01L 51/0052; H01L 51/0058; H01L 51/0061; H01L 51/0067; H01L 51/0072; H01L 51/0073; H01L 51/0085; H01L 51/50; H01L 51/5008; H01L 51/5016; H01L 51/5012; H01L 51/5056; H01L 51/0056; H01L 51/5072; C07C 211/54; C07C 211/61; C07C 2603/97; C07C 2603/18; C07D 209/82; C07D 209/86; C07D 251/24; C07D 307/91; C07D 403/04; C07D 403/10; C07D 405/14; C09K 11/06; C09K 2211/1007; C09K 2211/1011; C09K 2211/1014; C09K 2211/1018; C09K 2211/1029; C09K 2211/1033; C09K 2211/185

See application file for complete search history.

(56) References Cited

U.S. PATENT DOCUMENTS

| | | |
|---|---|---|
| 7,274,141 B2 | 9/2007 | Leo et al. |
| 8,604,689 B2 | 12/2013 | Ma et al. |
| 2004/0183082 A1 | 9/2004 | Yamazaki |
| 2005/0233166 A1 | 10/2005 | Ricks et al. |
| 2010/0301312 A1* | 12/2010 | Jinde .................. H01L 51/0059 257/40 |
| 2011/0057178 A1 | 3/2011 | Shitagaki et al. |
| 2011/0108810 A1 | 5/2011 | Kishino |
| 2013/0026452 A1* | 1/2013 | Kottas .................. H01L 51/50 257/40 |
| 2013/0126831 A1* | 5/2013 | Ma .................. H01L 51/0085 257/40 |

(Continued)

FOREIGN PATENT DOCUMENTS

| | | |
|---|---|---|
| CN | 1943057 A | 4/2007 |
| CN | 102082234 A | 6/2011 |

(Continued)

OTHER PUBLICATIONS

Lee, et al.: "High efficiency and non-color-changing orange organic light emitting diodes with red and green emitting layers", XP28554618, Organic Electronics, Elsevier, vol. 14, No. 7, Apr. 25, 2013, pp. 1856-1860.

(Continued)

*Primary Examiner* — Andrew K Bohaty
(74) *Attorney, Agent, or Firm* — Dentons US LLP

(57) ABSTRACT

The present disclosure provides an organic light emitting device having improved driving voltage, efficiency and life time.

13 Claims, 1 Drawing Sheet

(56) References Cited

U.S. PATENT DOCUMENTS

| | | | |
|---|---|---|---|
| 2013/0146850 A1 | 6/2013 | Pieh et al. | |
| 2013/0207046 A1* | 8/2013 | Pflumm | C07D 219/02 |
| | | | 252/500 |
| 2013/0240933 A1 | 9/2013 | Yamazaki et al. | |
| 2014/0042469 A1 | 2/2014 | Seo | |
| 2014/0145168 A1 | 5/2014 | Ohsawa et al. | |
| 2014/0217378 A1 | 7/2014 | Nishimura et al. | |
| 2014/0340888 A1 | 11/2014 | Ishisone et al. | |
| 2015/0065730 A1* | 3/2015 | Montenegro | C07D 307/91 |
| | | | 548/440 |
| 2015/0097161 A1 | 4/2015 | Song et al. | |
| 2015/0155511 A1 | 6/2015 | Ohsawa et al. | |
| 2015/0243905 A1* | 8/2015 | Yamamoto | C07D 403/14 |
| | | | 257/40 |
| 2015/0364696 A1 | 12/2015 | Park et al. | |
| 2016/0111644 A1 | 4/2016 | Cho et al. | |
| 2017/0077415 A1 | 3/2017 | Kim et al. | |
| 2017/0186965 A1* | 6/2017 | Parham | H01L 51/0073 |
| 2017/0207396 A1 | 7/2017 | Park et al. | |

FOREIGN PATENT DOCUMENTS

| | | | |
|---|---|---|---|
| CN | 102484923 A | 5/2012 | |
| CN | 102738410 A | 10/2012 | |
| CN | 103165817 A | 6/2013 | |
| CN | 103620808 A | 3/2014 | |
| CN | 104167494 A | 11/2014 | |
| JP | 2014056814 A | 3/2014 | |
| JP | 5972894 B2 | 8/2016 | |
| KR | 10-2000-0051826 A | 8/2000 | |
| KR | 10-2014-0133572 A | 11/2014 | |
| KR | 10-2015-0040118 A | 4/2015 | |
| KR | 10-2015-0111014 A | 10/2015 | |
| KR | 10-2015-0128590 A | 11/2015 | |
| KR | 10-2015-0138000 A | 12/2015 | |
| KR | 10-2015-0143963 A | 12/2015 | |
| KR | 10-2016-0011582 A | 2/2016 | |
| KR | 10-2016-0024625 A | 3/2016 | |
| KR | 10-2016-0027940 A | 3/2016 | |
| KR | 10-2016-0046075 A | 4/2016 | |
| KR | 10-2016-0078317 A | 7/2016 | |
| KR | 10-2016-0095319 A | 8/2016 | |
| KR | 10-1744248 B1 | 5/2017 | |
| TW | 201339123 A | 10/2013 | |
| TW | 201401602 A | 1/2014 | |
| WO | 2003-012890 A2 | 2/2003 | |
| WO | WO-2015169412 A1 * | 11/2015 | C07D 409/04 |
| WO | 2016013875 A1 | 1/2016 | |

OTHER PUBLICATIONS

Zhao et al.: "A hybrid white organic light-emitting diode with stable color and reduced efficiency roll-off by using a bipolar charge carrier switch", XP28856897, Organic Electronics, Elsevier, vol. 13, No. 6, Mar. 10, 2012, pp. 11049-1055.

* cited by examiner

[FIG. 1]
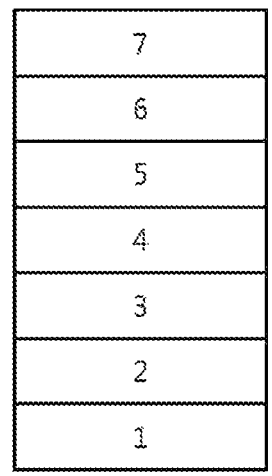
[FIG. 2]
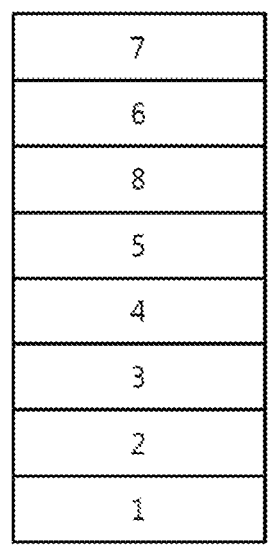

ORGANIC LIGHT EMITTING DEVICE

CROSS-REFERENCE TO RELATED APPLICATION

This application is the national stage of International Application No. PCT/KR2017/006722 filed on Jun. 26, 2017, and claims the benefit of Korean Application No. 10-2016-0114284 filed on Sep. 6, 2016, all of which are hereby incorporated by reference in their entirety for all purposes as if fully set forth herein.

TECHNICAL FIELD

The present disclosure relates to an organic light emitting device having improved driving voltage, efficiency and life time.

BACKGROUND OF ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode to the organic material layer, and when the injected holes and the electrons meet each other, an exciton is formed, and light is emitted when the exciton falls to a ground state again.

In the field of the organic light emitting device, development of an organic light emitting device having improved driving voltage, efficiency, and life time is continuously required.

PRIOR ART LITERATURE

Patent Literature (PATENT LITERATURE 1) Korean Patent Publication No. 10-2000-0051826

DETAILED DESCRIPTION OF THE INVENTION

Technical Problem

The present disclosure relates to an organic light emitting device having improved driving voltage, efficiency and life time.

Technical Solution

The present disclosure provides a following organic light emitting device:

An organic light emitting device comprising a first electrode; a hole transport layer; a first light emitting layer; a second light emitting layer; an electron transport layer; and a second electrode,
 wherein the first light emitting layer comprises a 1-1 host and a 1-2 host,
 the second light emitting layer comprises a 2-1 host and a 2-2 host,
 the hole transport layer comprises the same material as the 1-1 host, and
 the 1-2 host and the 2-1 host are the same materials.

Also, the present disclosure provides the organic light emitting device, further including a third light emitting layer between the second light emitting layer and the electron transport layer, wherein the third light emitting layer comprises a 3-1 host and a 3-2 host, and the 1-2 host, the 2-1 host and the 3-1 host are the same materials.

Advantageous Effects

The above-mentioned organic light emitting device has excellent driving voltage, efficiency and life time.

BRIEF DESCRIPTION OF DRAWINGS

FIG. 1 shows an example of an organic light emitting device including a substrate (1), an anode (2), a hole transport layer (3), a first light emitting layer (4), a second light emitting layer (5), an electron transport layer (6), and a cathode (7).

FIG. 2 shows an example of an organic light emitting device including a substrate (1), an anode (2), a hole transport layer (3), a first light emitting layer (4), a second light emitting layer (5), a third light emitting layer (8), an electron transport layer (6) and a cathode (7).

DETAILED DESCRIPTION OF THE EMBODIMENTS

Hereinafter, the present disclosure will be described in more detail to help understanding of the present invention.

In the present disclosure, means a bond connected to another substituent group.

As used herein, the term "substituted or unsubstituted" means that one or more substituent groups selected from the group consisting of deuterium; a halogen group; a nitrile group; a nitro group; a hydroxyl group; a carbonyl group; an ester group; an imide; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl groups; an aralkenyl group; an alkylaryl group; an alkylamine group; an aralkylamine group; a heteroarylamine group; an arylamine group; an arylphosphine group; or a heterocyclic group containing at least one of N, O, and S atoms are substituted or unsubstituted, or a substituent group where two or more substituent groups of the exemplified substituent groups are connected is substituted or unsubstituted. For example, the term "substituent group where two or more substituent groups are connected" may be a biphenyl group. That is, the biphenyl group may be an aryl group, or may be interpreted as a substituent group where two phenyl groups are connected.

In the present disclosure, the number of carbon atoms in a carbonyl group is not particularly limited, but 1 to 40 is preferable. Specifically, the carbonyl group may be a compound represented by following structures, but is not limited thereto.

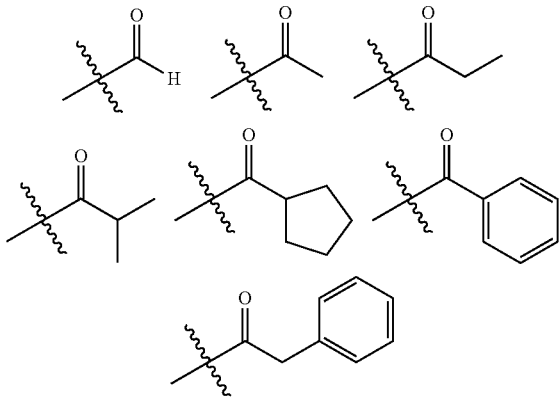

In the present disclosure, oxygen of an ester group may be substituted by a linear-chain, branched-chain, or cyclic alkyl group having 1 to 25 carbon atoms, or an aryl group having 6 to 25 carbon atoms. Specifically, the ester group may be a compound represented by following structures, but is not limited thereto.

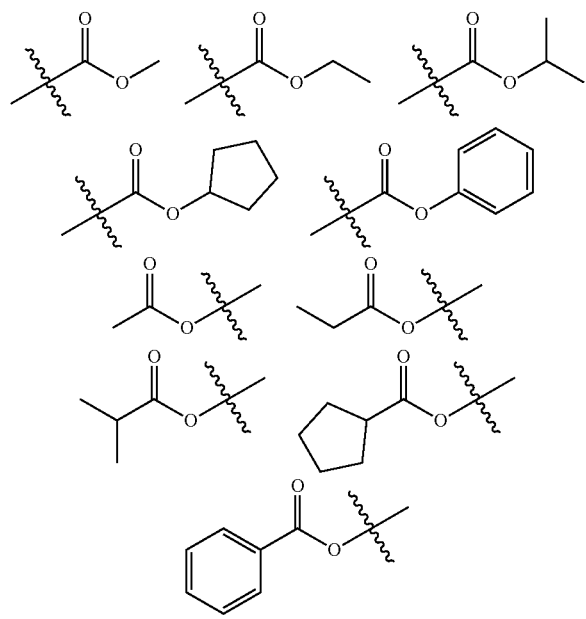

In the present disclosure, the number of carbon atoms in an imide group is not particularly limited, but 1 to 25 is preferable. Specifically, the imide group may be a compound represented by following structures, but is not limited thereto.

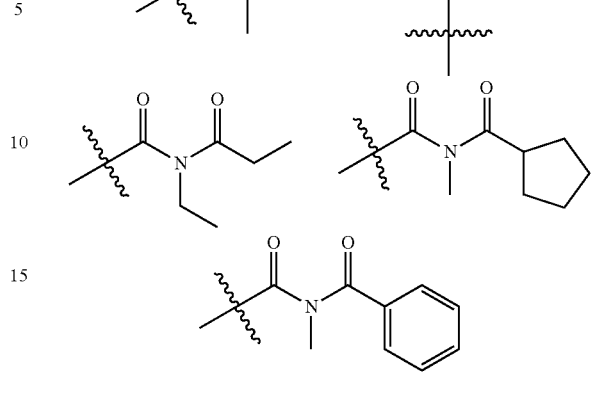

In the present disclosure, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, the boron group specifically includes a trimethylboron group, a triethylboron group, a t-butyldimethylboron group, a triphenylboron group, and a phenylboron group, and the like, but is not limited thereto.

In the present disclosure, examples of a halogen group include fluorine, chlorine, bromine, or iodine.

In the present disclosure, an alkyl group may be a linear chain or a branched chain, and the number of carbon atoms thereof is not particularly limited but is preferably 1 to 40. According to one embodiment, the alkyl group has 1 to 20 carbon atoms. According to another embodiment, the alkyl group has 1 to 10 carbon atoms. According to another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexcylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present disclosure, the alkenyl group may be a linear chain or a branched chain, and the number of carbon atoms thereof is not particularly limited but is preferably 2 to 40. According to one embodiment, the alkenyl group has 2 to 20 carbon atoms. According to another embodiment, the alkenyl group has 2 to 10 carbon atoms. According to another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group and a fluorenyl group or the like, but are not limited thereto.

In the present disclosure, a fluorenyl group may be substituted, and two substituent groups may be bonded to each other to form a spiro structure. In the case where the fluorenyl group is substituted,

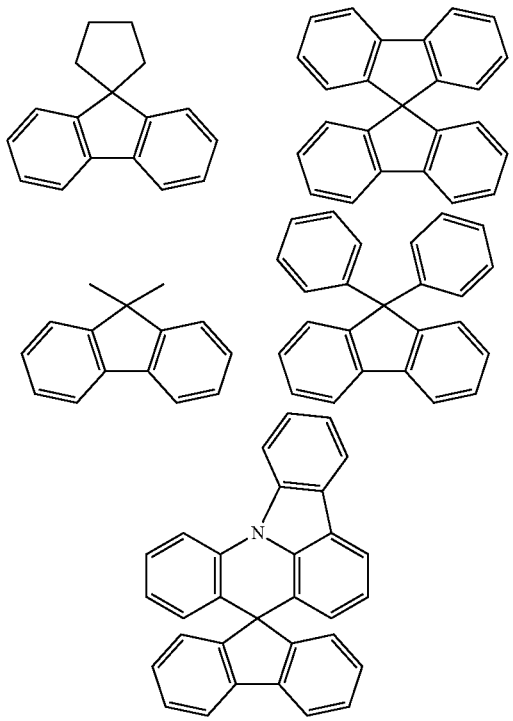

and the like can be formed. However, it is not limited thereto.

In the present disclosure, the heterocyclic group is a heterocyclic group including at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group, and the arylamine group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heteroaryl in the heteroarylamines can be applied to the above-mentioned description of the heterocyclic group. In the present disclosure, the alkenyl group in the aralkenyl group is the same as the above-mentioned examples of the alkenyl group. In the present disclosure, the above-mentioned description of the aryl group may be applied except that the arylene is a divalent group. In the present disclosure, the above-mentioned description of the heterocyclic group can be applied except that the heteroarylene is a divalent group. In the present disclosure, the above-mentioned description of the aryl group or cycloalkyl group can be applied except that the hydrocarbon ring is not a monovalent group but formed by combining two substituent groups. In the present disclosure, the above-mentioned description of the heterocyclic group can be applied, except that the heterocycle is not a monovalent group but formed by combining two substituent groups.

The present disclosure provides a following organic light emitting device:

An organic light emitting device comprising a first electrode; a hole transport layer; a first light emitting layer; a second light emitting layer; an electron transport layer; and a second electrode, wherein the first light emitting layer comprises a 1-1 host and a 1-2 host, the second light emitting layer comprises a 2-1 host and a 2-2 host, the hole transport layer comprises the same material as the 1-1 host, and the 1-2 host and the 2-1 host are the same materials.

The organic light emitting device according to the present disclosure is characterized in that it can improve driving voltage, efficiency and life time by controlling the energy level between the layers by controlling the materials included in the hole transport layer and the light emitting layer.

Hereinafter, the present disclosure will be described in detail with respect to each component.

The First Electrode and the Second Electrode

The first electrode and the second electrode used in the present disclosure are electrodes used in an organic light emitting device. For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

Also, a hole injection layer may be further included on the anode. The hole injection layer is made of a hole injection material, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability.

It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrile hexaazatriphenylene-based organic material, a quinacridone-based organic material, a perylene-based organic material, anthraquinone, polyaniline and polythiophene-based conductive polymer, and the like, but are not limited thereto.

In addition, an organic layer may be further included between the first electrode and the hole transport layer, and/or between the second electrode and the electron transport layer. The organic layer also includes a light emitting layer.

The Hole Transport Layer, the First Light Emitting Layer, the Second Light Emitting Layer The hole transport layer of the present disclosure is a layer receiving the holes from the hole injection layer which is formed in or on the anode, and transporting the holes to the light emitting layer. For the hole transport material, a material which can receive the holes from the anode or the hole injection layer and transport the holes to the light emitting layer, a material having large mobility to the holes, is suitable.

Particularly, in the organic light emitting device of the present disclosure, it is preferable that the hole transport layer and the first light emitting layer are in contact with each other, and the same material as the 1-1 host included in the first light emitting layer is used as the hole transport material.

When a plurality of light emitting layers are provided as in the organic light emitting device of the present disclosure, the first light emitting layer positioned on the anode side should serve as a hole transporting layer for injecting holes into the second light emitting layer. In order to move the holes to the second light emitting layer, holes coming from the anode should be transported without any loss. For this, it is preferable that one of the materials constituting the host of the first light emitting layer is made of the same material as the material included in the hole transport layer. In this case, the interface resistance between the hole transport layer and the first light emitting layer may be reduced, the holes may be more easily introduced into the first light emitting layer, and the amount of holes transported to the second light emitting layer may be increased, thereby increasing the luminous efficiency of the organic light emitting device and preventing the increase of the driving voltage generally. Further, by using a material having excellent hole transporting properties as one of the hosts of the first light emitting layer, the hole transporting property of the first light emitting layer itself may be improved. Further, as providing a sufficient amount of holes to be used to perform a hole trap by the dopant of the first light emitting layer, it is possible to provide sufficient holes necessary for improving the luminous efficiency in the first light emitting layer and the second light emitting layer.

As the hole transport material and the 1-1 host, a compound represented by a following Chemical Formula 1 may be used:

[Chemical Formula 1]

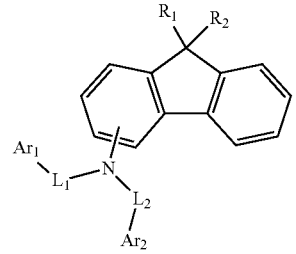

in Chemical Formula 1, $R_1$ and $R_2$ are each independently hydrogen; deuterium; halogen; nitrile; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heterocyclic group containing at least one of O, N, Si and S, $L_1$ and $L_2$ are each independently a bond, or a substituted or unsubstituted $C_{6-60}$ arylene, and $Ar_1$ and $Ar_2$ are each independently a substituted or unsubstituted $C_{6-60}$ aryl; or a substituted or unsubstituted $C_{2-60}$ heteroaryl containing at least one of O, N, Si and S.

Preferably, $R_1$ and $R_2$ are each independently a substituted or unsubstituted $C_{1-60}$ alkyl, and more preferably, methyl.

Preferably, $L_1$ and $L_2$ are each independently a bond, or phenylene.

Preferably, $Ar_1$ and $Ar_2$ are each independently, biphenylyl,

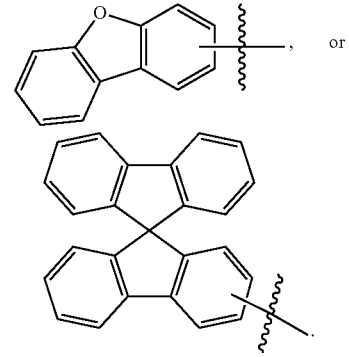

More preferably, $Ar_1$ is biphenylyl, and $Ar_2$ is

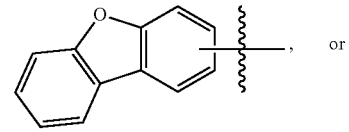

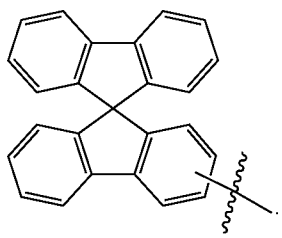
Preferably, the compound represented by the Chemical Formula 1 may be any one selected from the group consisting of:
1-1
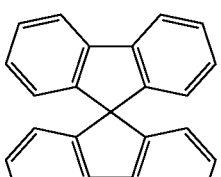
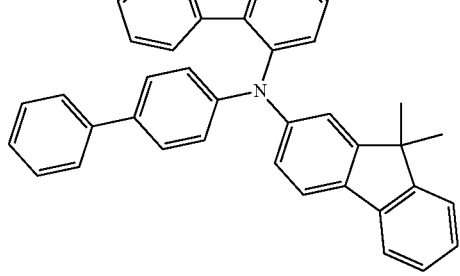
1-2
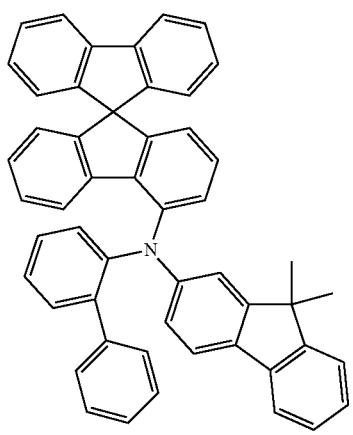
1-3
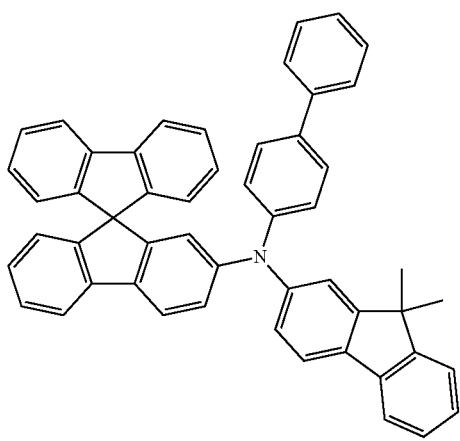
1-4
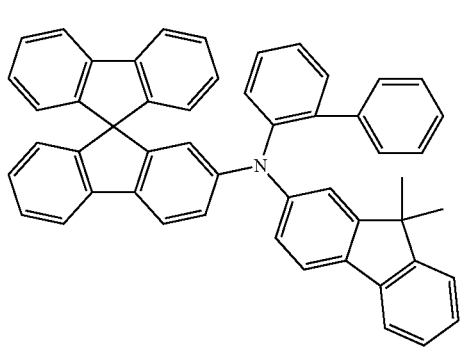
1-5
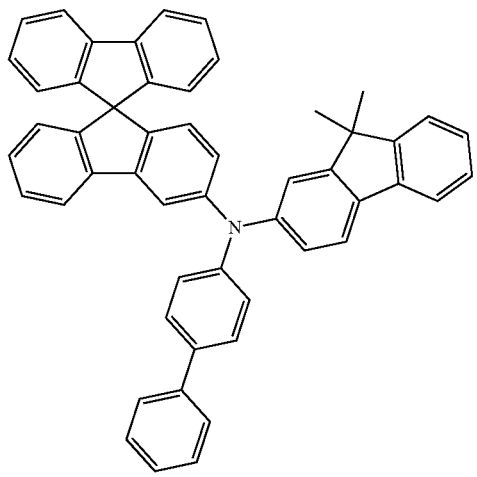
1-6
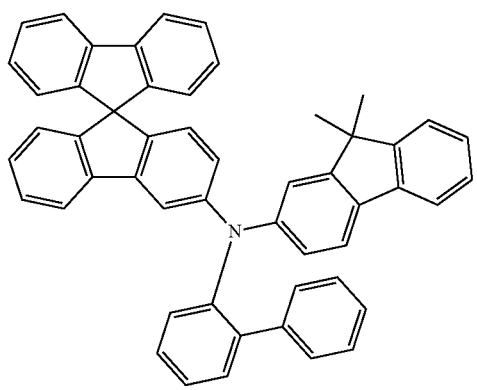

1-7
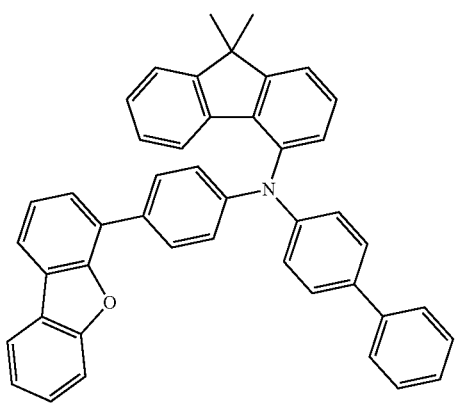
1-8
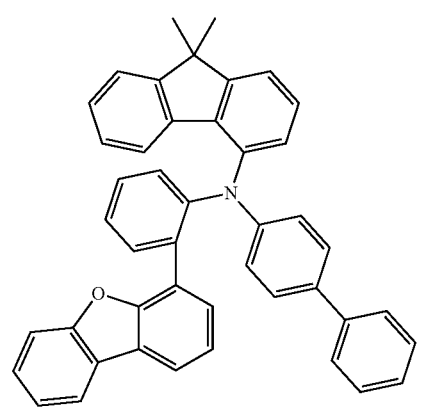
1-9
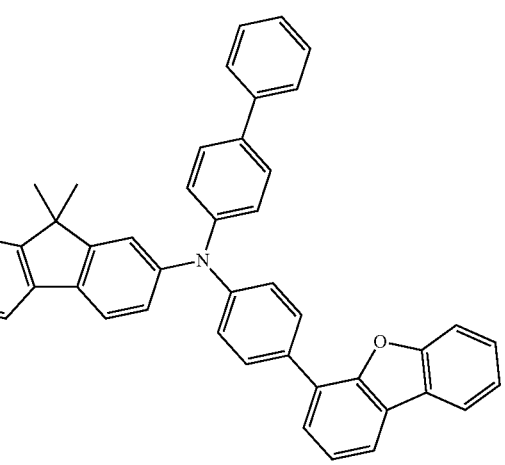
1-10
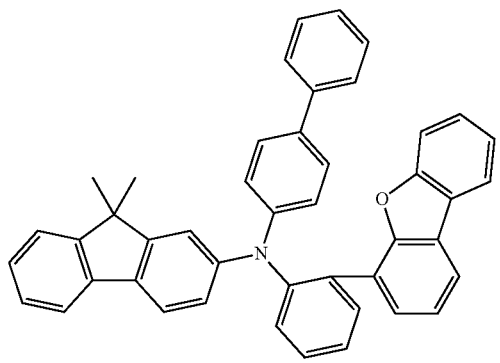
1-11
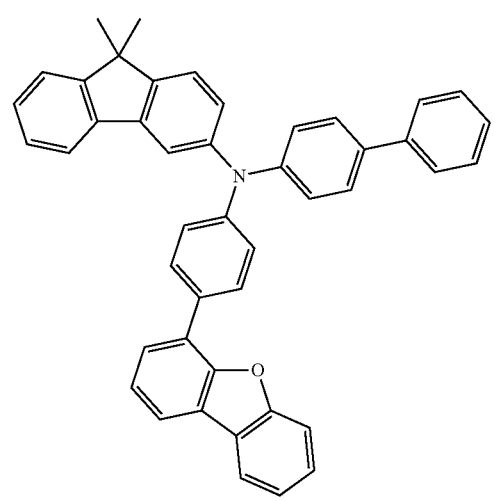
1-12
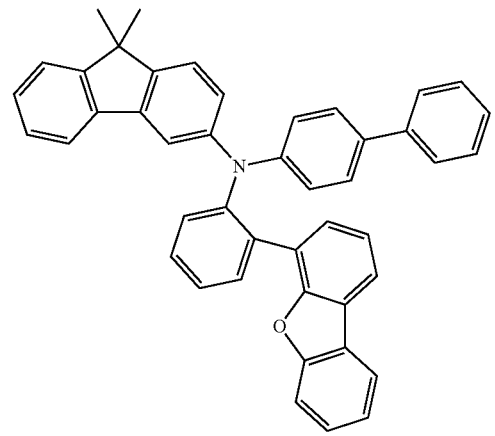
The compound represented by the Chemical Formula 1 may be prepared as in following Reaction Formula 1:
[Reaction Formula 1]
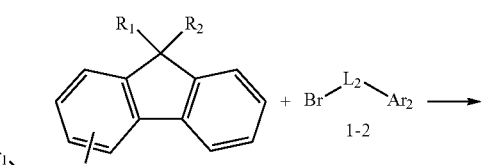

-continued

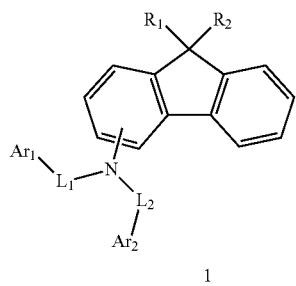

(In Reaction Formula 1, $R_1$, $R_2$, $L_1$, $L_2$, $Ar_1$, and $Ar_2$ are the same as defined in Chemical Formula 1)

Specifically, the compound represented by the Chemical Formula 1 may be prepared by a process including the step of reacting the compound represented by the Chemical Formula 1-1 with the compound represented by the Chemical Formula 1-2. The preparation method will be described more specifically in the following Examples.

Alternatively, as the hole transport material and the 1-1 host, a compound represented by a following Chemical Formula 1' may be used:

[Chemical Formula 1']

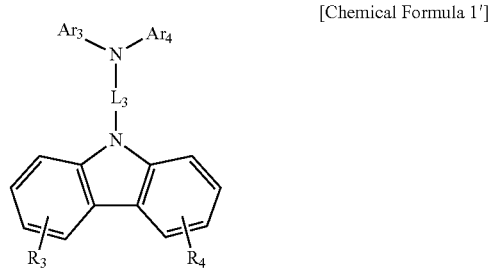

in Chemical Formula 1', $R_3$ and $R_4$ are each independently hydrogen; deuterium; halogen; nitrile; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heterocyclic group containing at least one of O, N, Si and S, $L_3$ is a bond, or a substituted or unsubstituted $C_{6-60}$ arylene, and $Ar_3$ and $Ar_4$ are each independently a substituted or unsubstituted $C_{6-60}$ aryl; or a substituted or unsubstituted $C_{2-60}$ heteroaryl containing at least one of O, N, Si and S.

Preferably, $R_3$ and $R_4$ are hydrogen.

Preferably, $L_3$ is biphenylylene.

Preferably, $Ar_3$ and $Ar_4$ are biphenylyl.

Preferably, the compound represented by the Chemical Formula 1' may be a following compound:

1-13

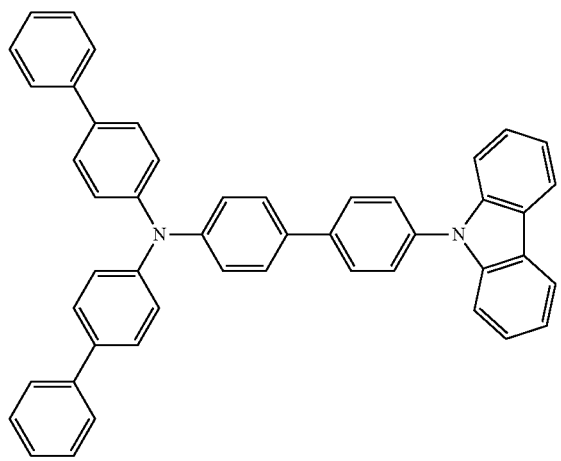

The preparation method of the compound will be described more specifically in the following Examples.

Also, in addition to the fact that the hole transport material and the 1-1 host included in the first light emitting layer are the same, the 1-2 host included in the first light emitting layer and the 2-1 host included in the second light emitting layer are the same. That is, the hole transport layer, the first light emitting layer and the second light emitting layer are sequentially laminated, and the 1-2 host included in the first light emitting layer and the 2-1 host included in the second light emitting layer use the same material.

As described above, since the first light emitting layer comprises the same material as the hole transport layer, the holes may be sufficiently supplied to the first light emitting layer. However, in order to improve the overall luminous efficiency of the organic light emitting device, the electrons should easily enter the first light emitting layer through the second light emitting layer. To this end, by including the material that the same as the host of the second light emitting layer and different from the hole transport layer of the first light emitting layer, the balance between the electrons and the holes in the first light emitting layer may be appropriately adjusted to increase the luminous efficiency. In addition, when the electrons are injected from the second light emitting layer to the first light emitting layer, the electrons move through the same material, so that the interface resistance between the first light emitting layer and the second light emitting layer is reduced and the driving voltage may be lowered.

As the 1-2 host, a compound represented by a following Chemical Formula 2 may be used:

[Chemical Formula 2]

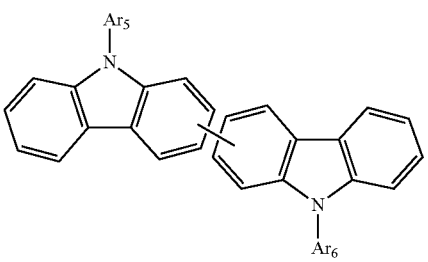

in Chemical Formula 2, $Ar_5$ and $Ar_6$ are each independently a substituted or unsubstituted $C_{6-60}$ aryl.

Preferably, the compound represented by the Chemical Formula 2 may be any one selected from the group consisting of:
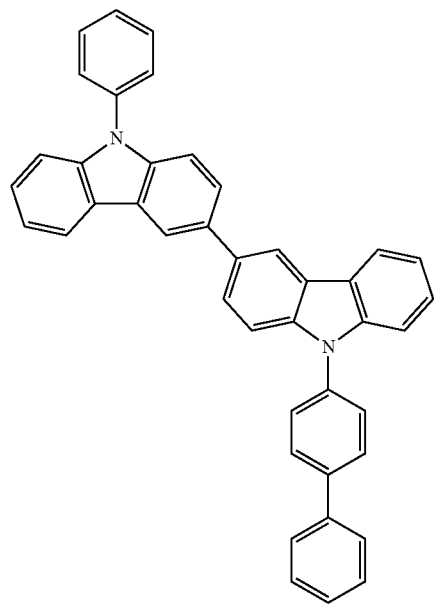
2-1
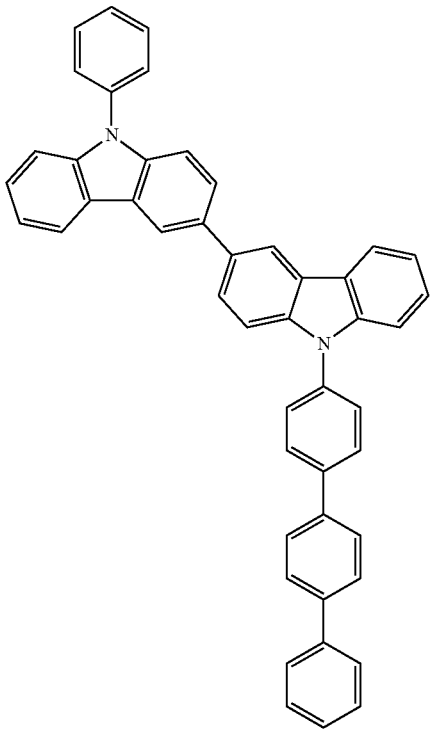
2-3
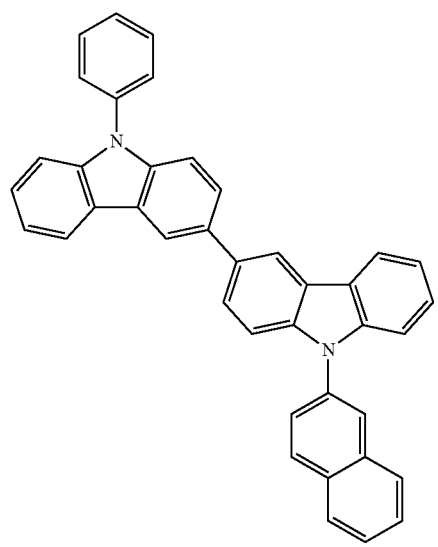
2-2
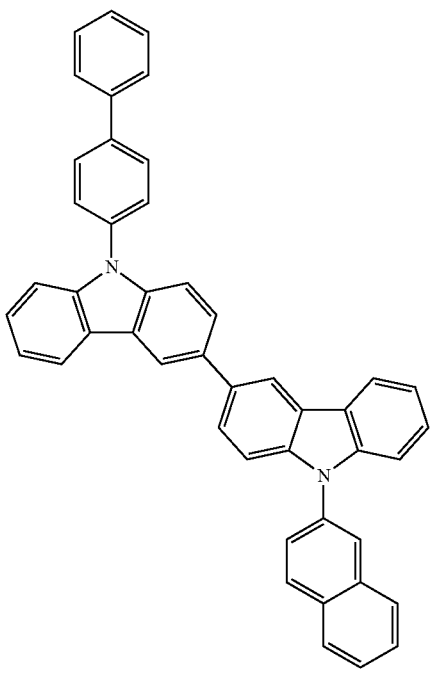
2-4

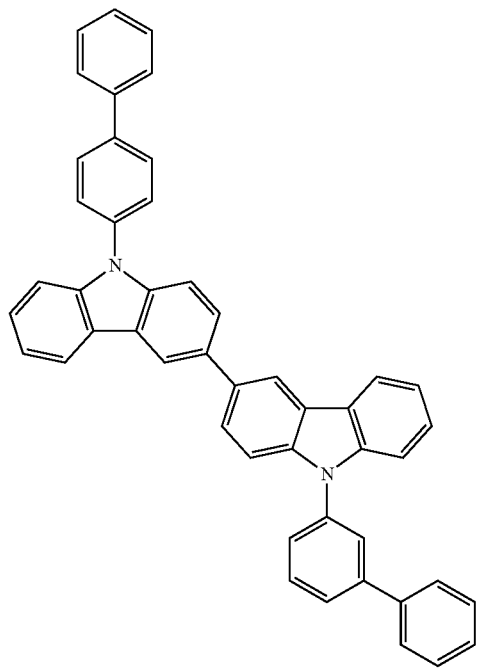
2-5
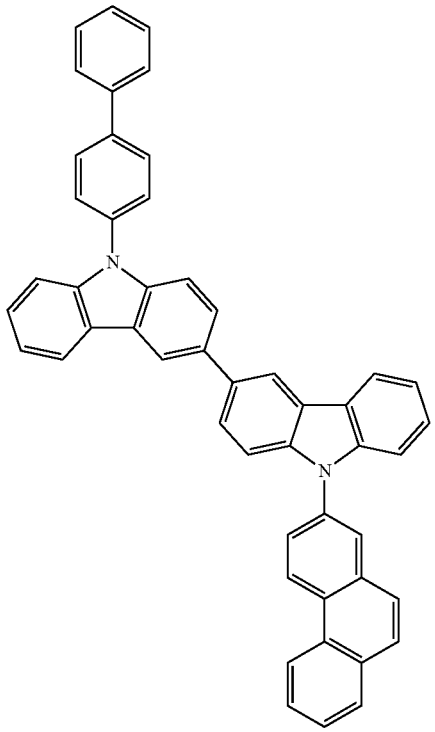
2-7
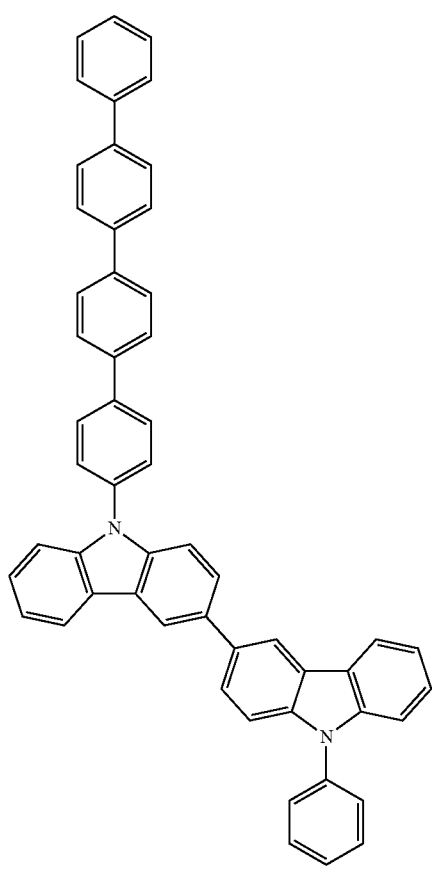
2-6
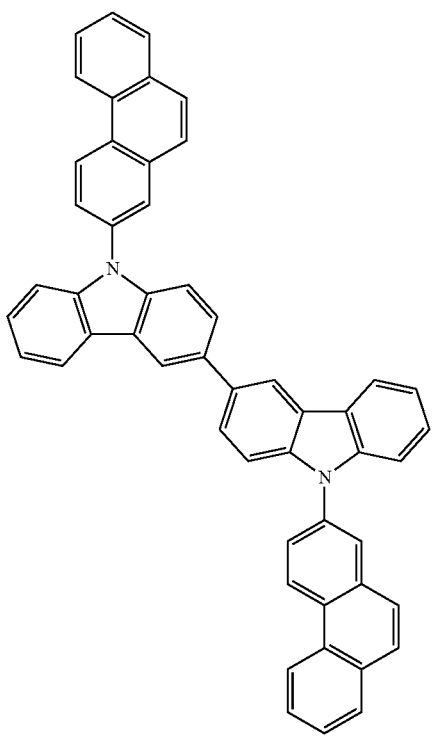
2-8

2-9
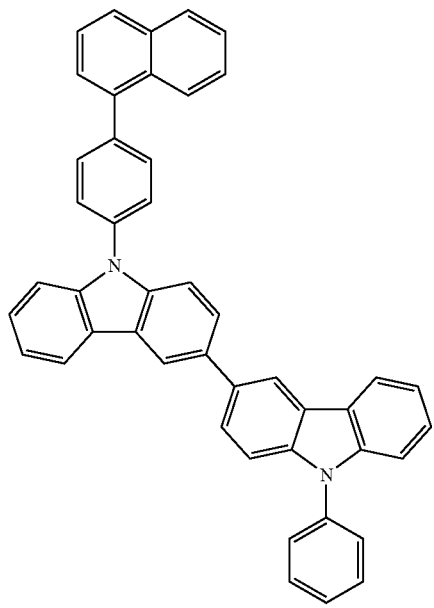
2-10
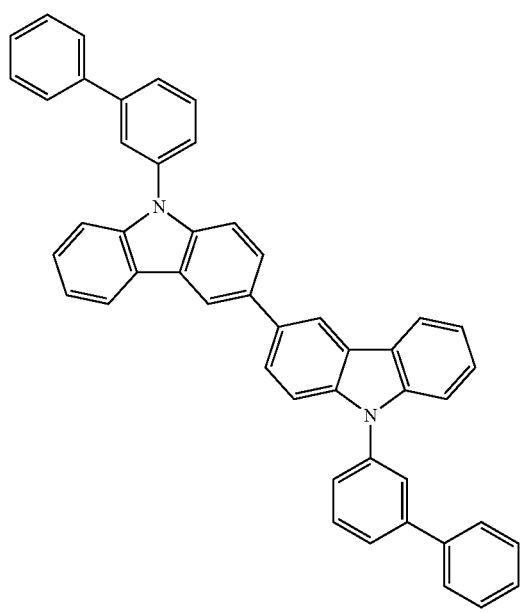
2-11
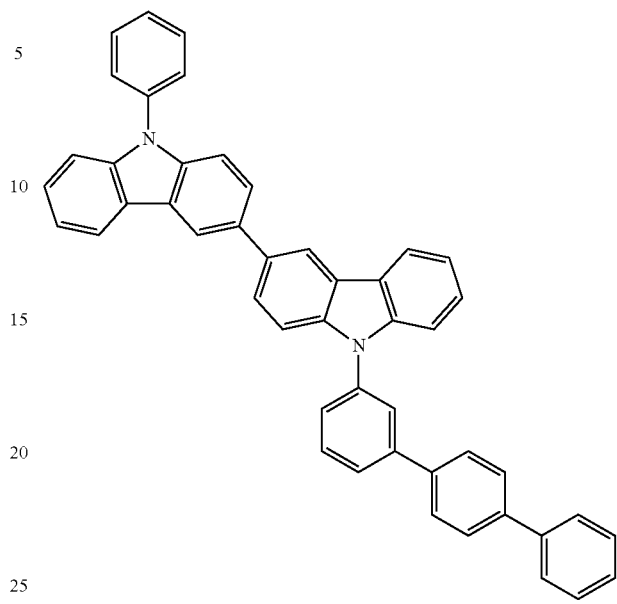
2-12
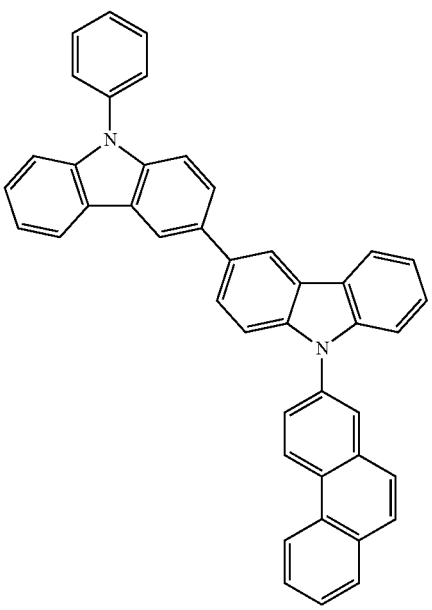

2-13
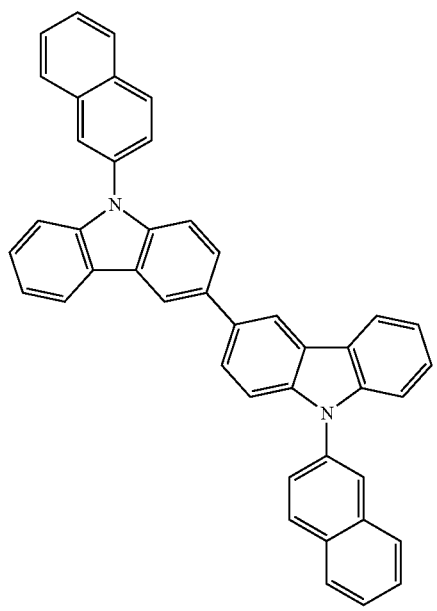
2-14
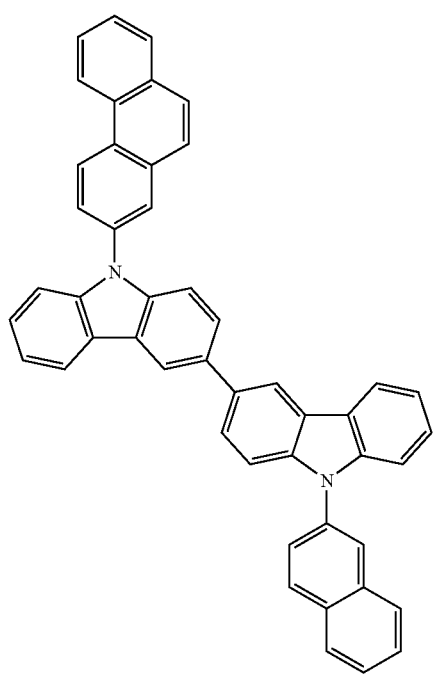
2-15
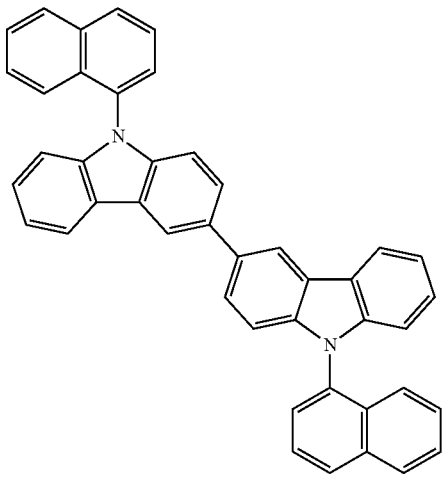
2-16
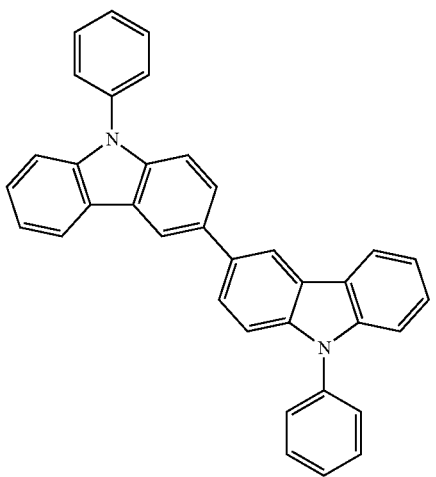

2-17
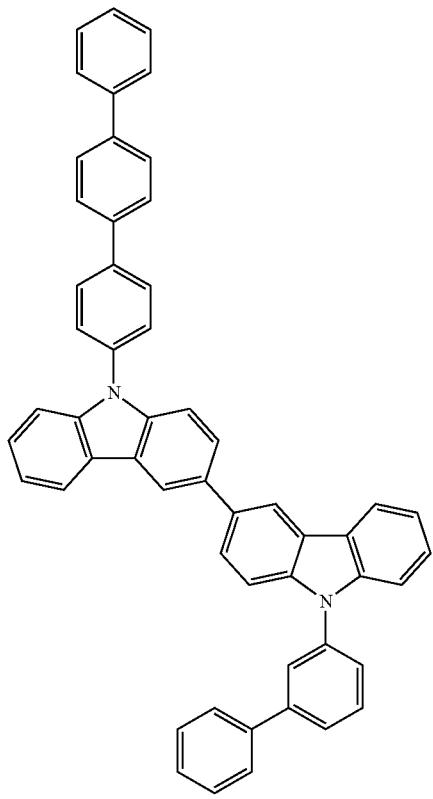
2-18
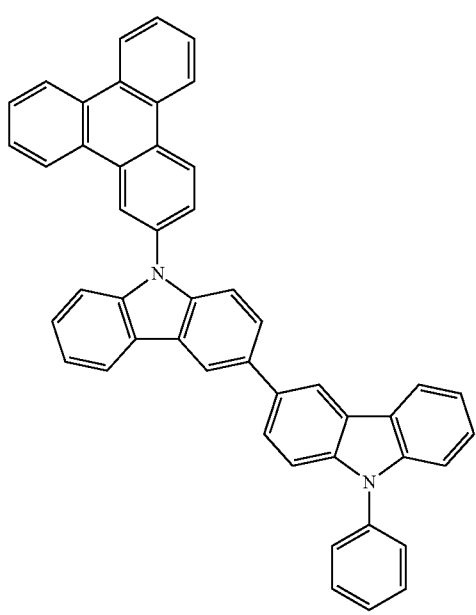
2-19
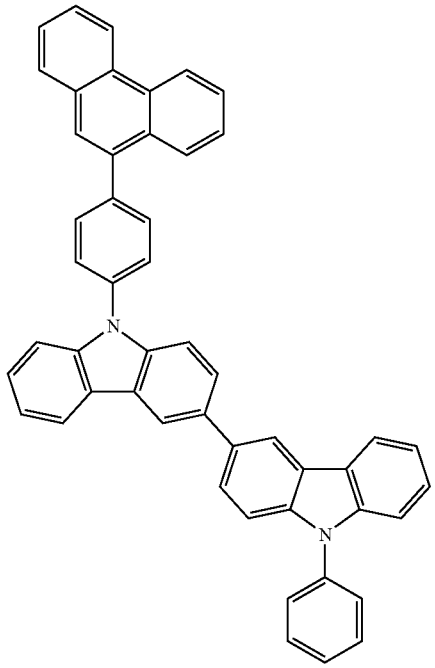
2-20
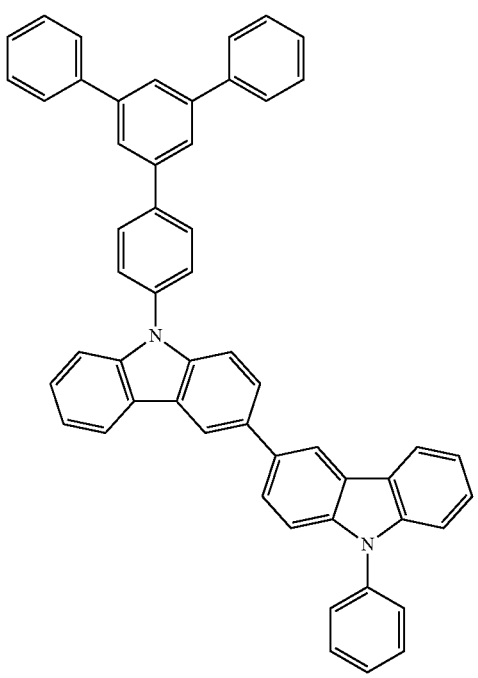

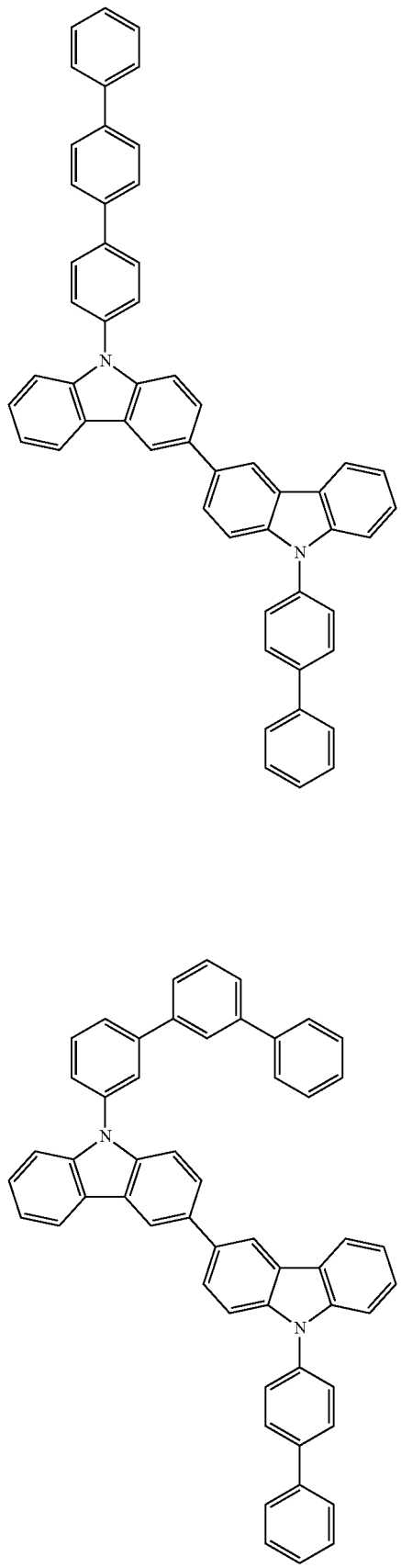
2-21
2-22
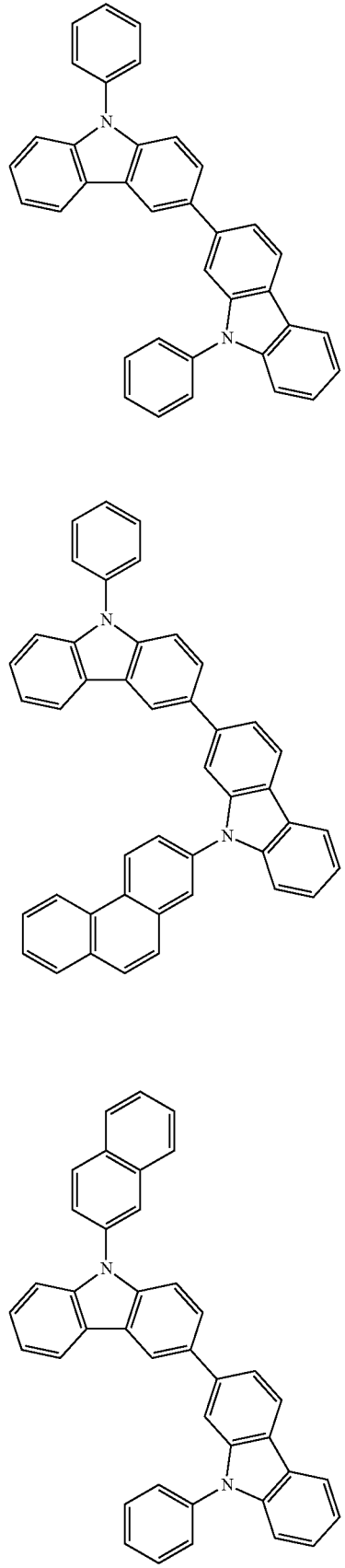
2-23
2-24
2-25

2-26
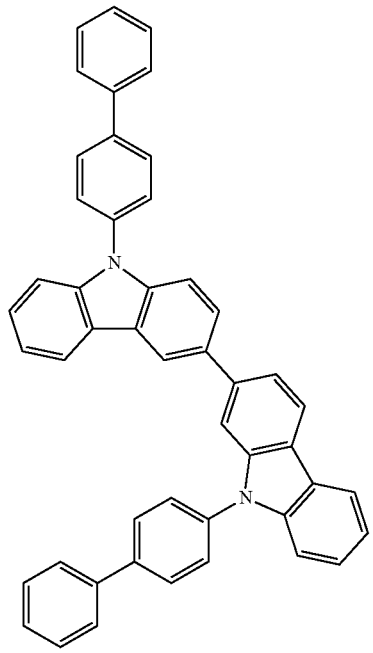
2-28
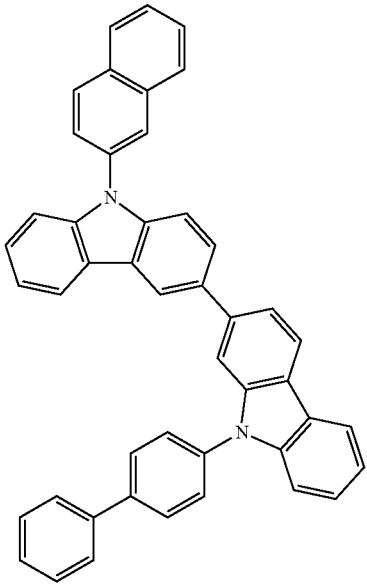
2-27
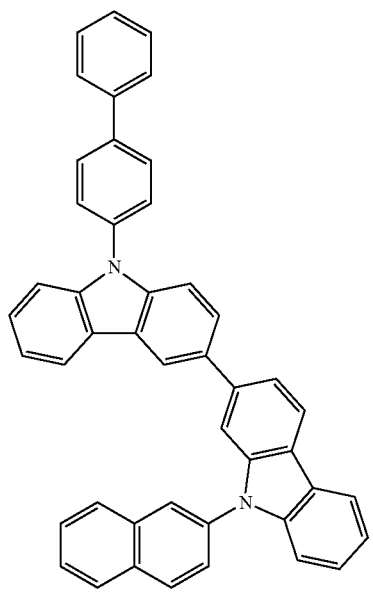
2-29

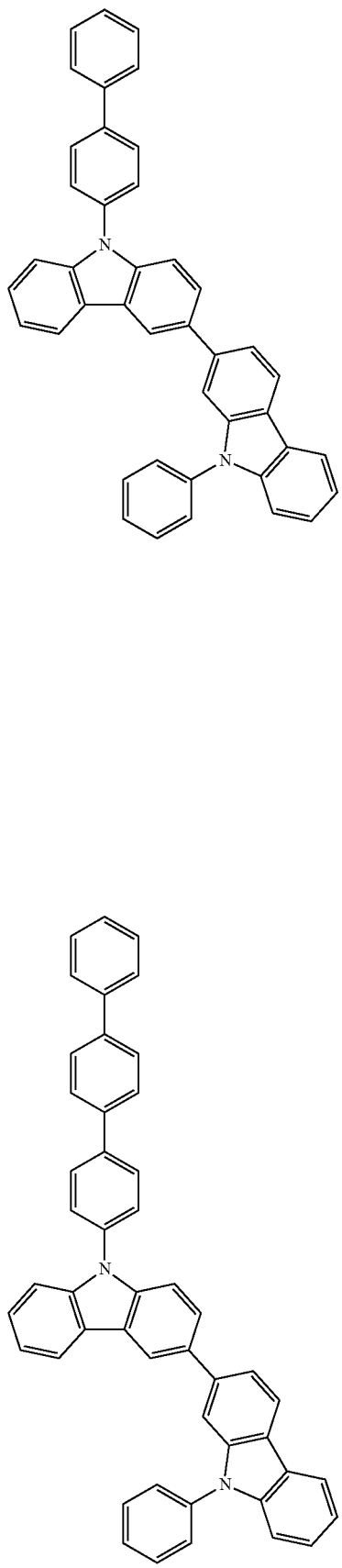
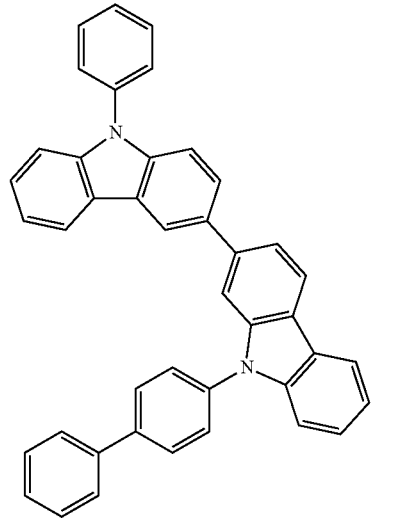
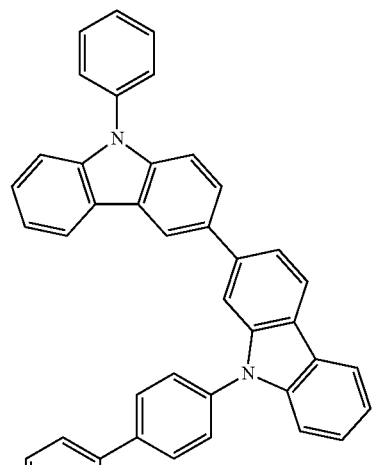
The compound represented by the Chemical Formula 2 may be prepared as in following Reaction Formula 2:
[Reaction Formula 2]
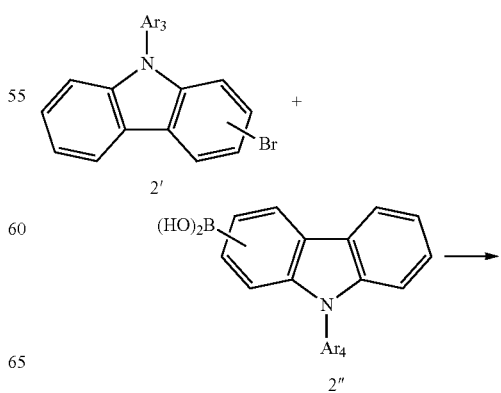

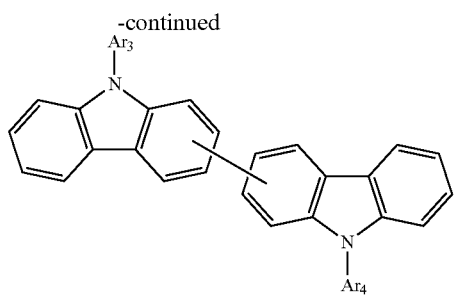

(In Reaction Formula 2, $Ar_3$ and $Ar_4$ are the same as defined in Chemical Formula 2)

Specifically, the compound represented by the Chemical Formula 2 may be prepared by a process including the step of reacting the compound represented by the Chemical Formula 2' with the compound represented by the Chemical Formula 2". The preparation method will be described more specifically in the following Examples.

As described above, the first light emitting layer comprises two kinds of hosts, and one of the hosts is the same as the material of the hole transport layer and the other is the same as the second light emitting layer.

Also, the second light emitting layer of the present disclosure may further comprise one kind of the host other than the 2-1 host, that is, the 2-2 host. As the 2-2 host, a compound represented by a following Chemical Formula 3 may be used.

[Chemical Formula 3]

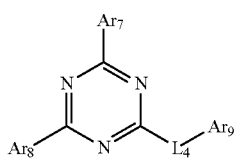

in Chemical Formula 3, $L_4$ is a bond; a substituted or unsubstituted $C_{6-60}$ arylene; or a substituted or unsubstituted $C_{2-60}$ heteroarylene containing at least one of O, N, Si and S, $Ar_7$ and $Ar_8$ are each independently a substituted or unsubstituted $C_{6-60}$ aryl; or a substituted or unsubstituted $C_{2-60}$ heteroaryl containing at least one of O, N, Si and S, and $Ar_9$ is a substituted or unsubstituted $C_{2-60}$ heteroaryl containing at least one N.

Preferably, $L_4$ is phenylene, or dibenzofurandiyl.

Preferably, $Ar_7$ and $Ar_8$ are phenyl.

Preferably, $Ar_9$ is any one selected from the group consisting of:

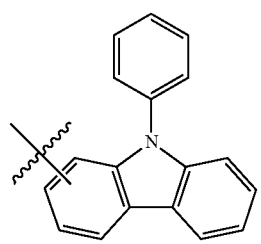

Preferably, the compound represented by the Chemical Formula 3 may be any one selected from the group consisting of:

3-1

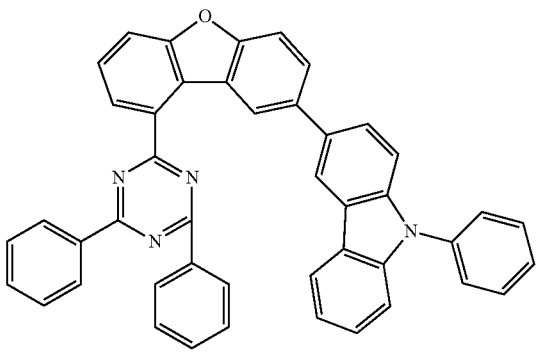

3-2

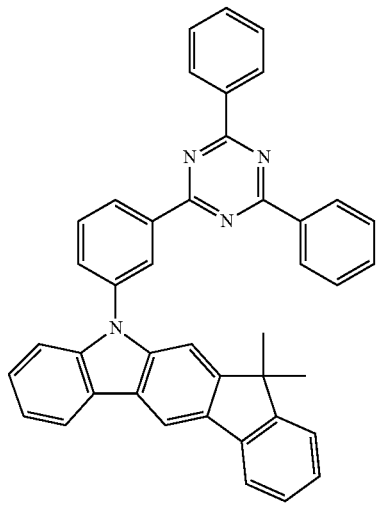

The preparation method of the compound will be described more specifically in the following Examples.

In the mean time, the first light emitting layer is preferably a red light emitting layer. For this, the first light emitting layer preferably comprises a red phosphorescent dopant. The red phosphorescent dopant is not particularly limited as long as it is a red phosphorescent dopant used in an organic light emitting device. For example, the first light emitting layer may further comprise a compound represented by a following formula 4:

[Chemical Formula 4]

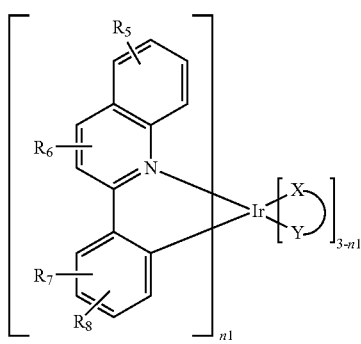

in Chemical Formula 4, n1 is 1 or 2, $R_5$ to $R_8$ are each independently hydrogen; a substituted or unsubstituted $C_{1-60}$ alkyl; or a substituted or unsubstituted $C_{6-60}$ aryl; provided that one or more of $R_5$ to $R_8$ are a branched alkyl containing 4 or more carbons, and X—Y is an auxiliary ligand.

Preferably, n1 is 2.

Preferably, $R_5$ is isobutyl. Preferably, $R_6$ is hydrogen. Preferably, $R_7$ and $R_8$ are methyl.

Preferably, X—Y is acetylacetonate.

Preferably, the compound represented by the Chemical Formula 4 may be a following compound.

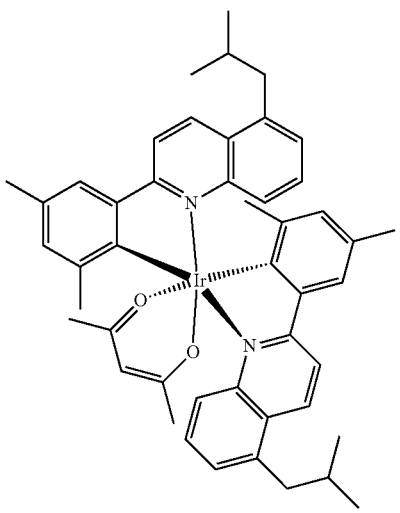

Also, the second light emitting layer is preferably a yellowish green light emitting layer. For this, the second light emitting layer preferably comprises a yellowish green phosphorescent dopant. The yellowish green phosphorescent dopant is not particularly limited as long as it is a yellowish green phosphorescent dopant used in an organic light emitting device. For example, the second light emitting layer may further comprise a compound represented by a following formula 5:

[Chemical Formula 5]

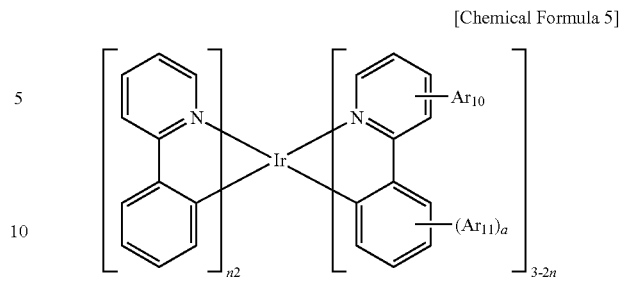

in Chemical Formula 5, n2 is 1 or 2, a is an integer of 0 to 4, and $Ar_{10}$ and $Ar_{11}$ are each independently a substituted or unsubstituted $C_6$-60 aryl; or a substituted or unsubstituted $C_{2-60}$ heteroaryl containing at least one of O, N, Si and S.

Preferably, n2 is 2.

Preferably, a is 0.

Preferably, $Ar_{10}$ and $Ar_{11}$ are each independently phenyl.

Preferably, the compound represented by the Chemical Formula 5 may be a following compound.

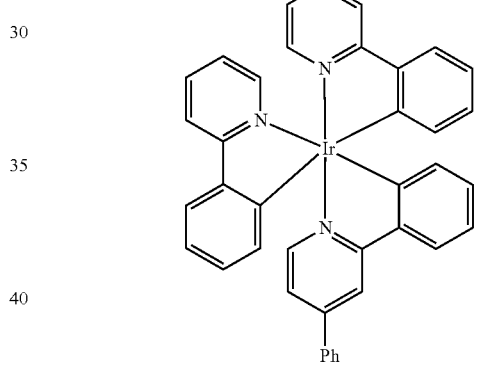

The Third Light Emitting Layer

The organic light emitting device of the present disclosure may further comprise the third light emitting layer. Preferably, the organic light emitting device of the present disclosure may have a structure that the hole transport layer, the first light emitting layer, the second light emitting layer and the third light emitting layer are sequentially laminated.

Particularly, the third light emitting layer comprises the 3-1 host and the 3-2 host. Further, the same material is used for the 1-2 host, the 2-1 host and the 3-1 host.

The first light emitting layer should have a role of injecting holes and the third light emitting layer should have a role of injecting electrons around the second light emitting layer. As described above, the first light emitting layer contains the same material as the material included in the hole transport layer which is excellent in hole transport. In addition, since the first light emitting layer is farthest from the cathode, it is preferable that the third light emitting layer comprises the same material as the second light emitting layer in order to smoothly provide electrons. Since the second light emitting layer is located closer to the cathode than the first light emitting layer, it is necessary to transport electrons well, but the charge balance may be adjusted to improve efficiency by including a material having bipolar characteristic. Further, since the same material is included in two or more light emitting layers, there is also an effect of lowering the driving voltage by reducing the interfacial resistance between light emitting layers.

In addition, the third light emitting layer of the present disclosure may further comprise one kind of the host other than the 3-1 host, that is, the 3-2 host. As the 3-2 host, a compound represented by a following Chemical Formula 3 may be used.

The 3-2 host may use a compound represented by a following Chemical Formula 3.

[Chemical Formula 3]

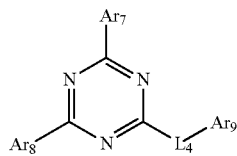

in Chemical Formula 3, $L_4$ is a bond; a substituted or unsubstituted $C_{6-60}$ arylene; or a substituted or unsubstituted $C_{2-60}$ heteroarylene containing at least one of O, N, Si and S, $Ar_7$ and $Ar_8$ are each independently a substituted or unsubstituted $C_{6-60}$ aryl; or a substituted or unsubstituted $C_{2-60}$ heteroaryl containing at least one of O, N, Si and S, and $Ar_9$ is a substituted or unsubstituted $C_{2-60}$ heteroaryl containing at least one N.

Preferably, $L_4$ is phenylene, or dibenzofurandiyl.

Preferably, $Ar_7$ and $Ar_8$ are phenyl.

Preferably, $Ar_9$ is any one selected from the group consisting of:

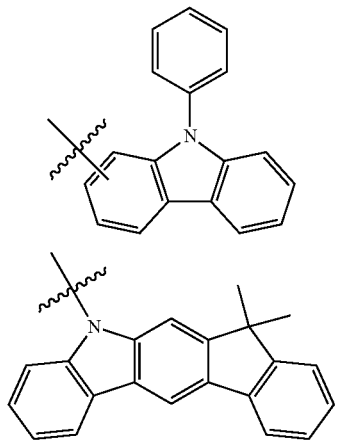

Preferably, the compound represented by the Chemical Formula 3 may be any one selected from the group consisting of:

3-1

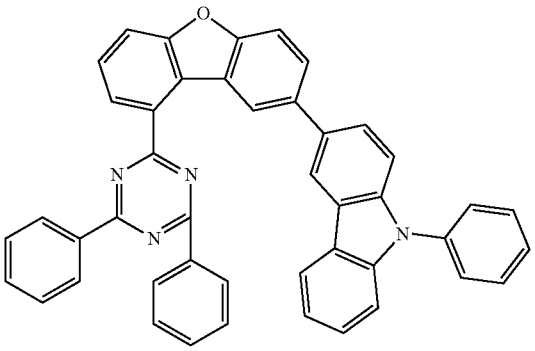

3-2

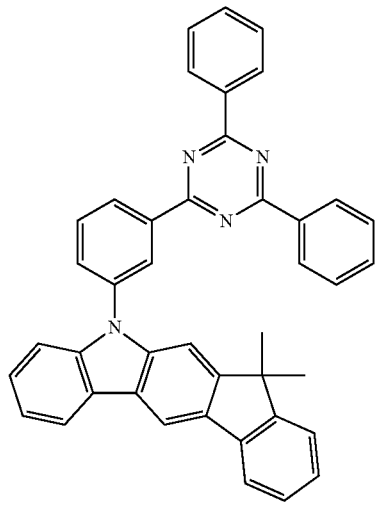

The preparation method of the compound will be described more specifically in the following Examples.

In the mean time, the third light emitting layer is preferably a green light emitting layer. For this, the third light emitting layer preferably comprises a green phosphorescent dopant. The green phosphorescent dopant is not particularly limited as long as it is a green phosphorescent dopant used in an organic light emitting device. For example, the third light emitting layer may further comprise a compound represented by a following Chemical Formula 6:

[Chemical Formula 6]

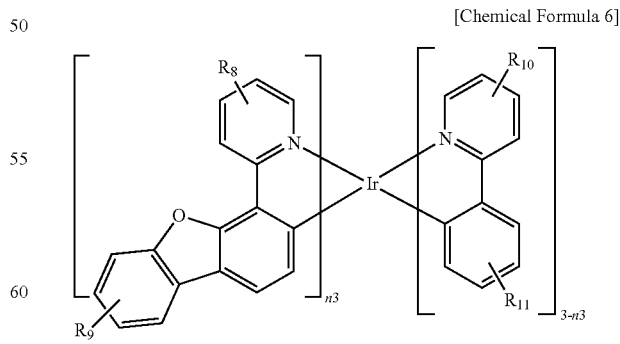

in Chemical Formula 6, n3 is 1 or 2, and $R_8$ to $R_{11}$ are each independently hydrogen; deuterium; halogen; nitrile; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heterocyclic group containing at least one of O, N, Si and S.

Preferably, n3 is 1.

Preferably, $R_8$ to $R_{11}$ are each independently hydrogen, or $CD_3$.

Preferably, $R_8$ is hydrogen, and $R_9$ to $R_{11}$ are $CD_3$.

Preferably, the compound represented by the Chemical Formula 6 may be a following compound.

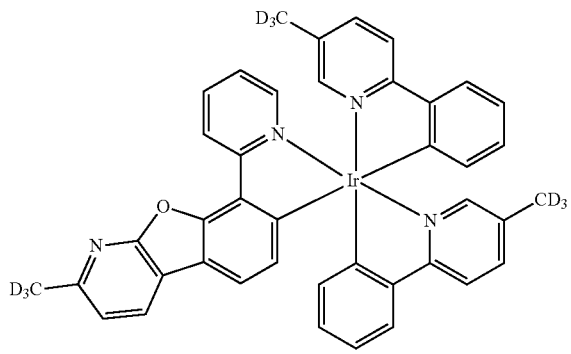

The Electron Transport Layer

The electron transport material of the present disclosure is a layer receiving the electrons from the electron injection layer which is formed in or on the cathode, and transporting the electrons to the light emitting layer. For the electron transport material, a material which can receive the electrons well from the cathode and transport the electrons to the light emitting layer, a material having large mobility to the electrons, is suitable.

Specific examples of the electron transport material include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The Electron Injection Layer

The organic light emitting device of the present disclosure may further comprise the electron injection layer between the electron transport layer and the cathode. The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable.

Specific examples of the material for the electron injection layer include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The Organic Light Emitting Device

The structure of the organic light emitting device according to the present disclosure is illustrated in FIG. 1. FIG. 1 illustrates an example of an organic light emitting device including a substrate (1), an anode (2), a hole transport layer (3), a first light emitting layer (4), a second light emitting layer (5), an electron transport layer (6), and a cathode (7).

Also, another structure of the organic light emitting device according to the present disclosure is illustrated in FIG. 2. FIG. 2 illustrates an example of an organic light emitting device including a substrate (1), an anode (2), a hole transport layer (3), a first light emitting layer (4), a second light emitting layer (5), a third light emitting layer (8), an electron transport layer (6) and a cathode (7).

The organic light emitting device according to the present disclosure may be manufactured by sequentially laminating the above mentioned components. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material which can be used as the cathode thereon. In addition to such a method, the organic light emitting device may be manufactured by sequentially depositing a cathode material, the organic material layer, and an anode material on the substrate. Further, the light emitting layer may be formed using the host and the dopant by a solution coating method as well as a vacuum deposition method. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

Meanwhile, the organic light emitting device according to the present disclosure may be a front side emission type, a back side emission type, or a double side emission type according to the used material.

Hereinafter, the preferred Examples are provided for better understanding. However, these Examples are for illustrative purposes only, and the present invention is not intended to be limited by these Examples.

Preparation Example 1

1) Preparation of Compound 1-1

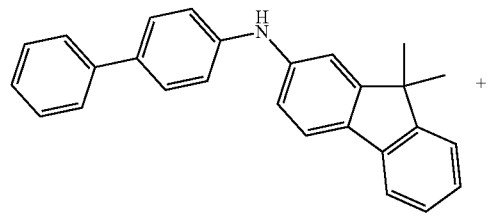

A lp;1p

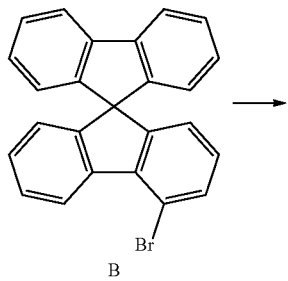

B

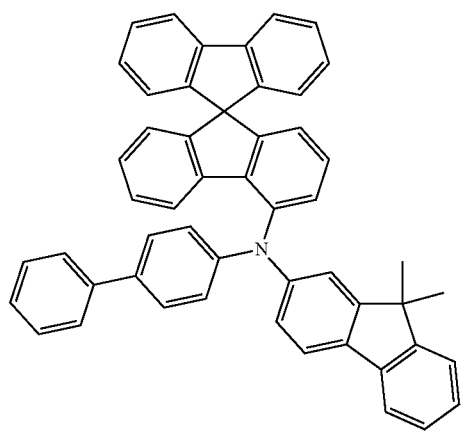

1-1

To the deaerated toluene (500 mL), Compound represented by A (144 mmol), Compound represented by B (111 mmol), tri-tert-butylphosphine (4.4 mmol), palladium acetate (1.1 mmol) and sodium tert-butoxide (166 mmol) were added, and the mixture was heated under reflux for 2 hours. The reaction mixture was cooled down to room temperature, increased with toluene and filtered through celite. The filtrate was evaporated under vacuum and the residue was crystallized from ethyl acetate/heptane. The crude product was extracted from a Soxhlet extractor (toluene) and purified by sublimation under vacuum.

MS: [M+H]+=676

Hereinafter, following compounds were prepared in the same manner as in the preparation of Compound 1-1, except that the Compound represented by A and the Compound represented by B were changed to correspond to the compound structure to be prepared.

2) Preparation of Compound 1-7

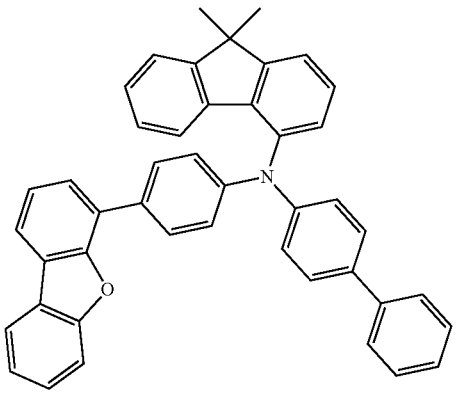

1-7

MS: $[M + H]^+ = 604$

3) Preparation of Compound 1-8

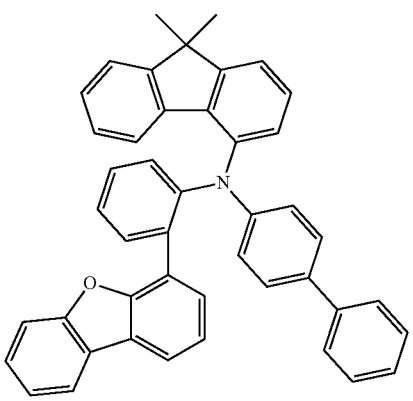

1-8

MS: $[M + H]^+ = 604$

4) Preparation of Compound 1-13

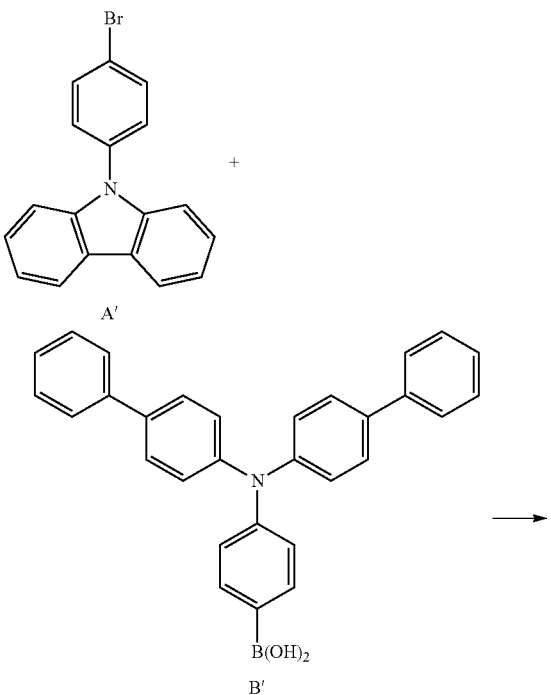

A'

B'

-continued

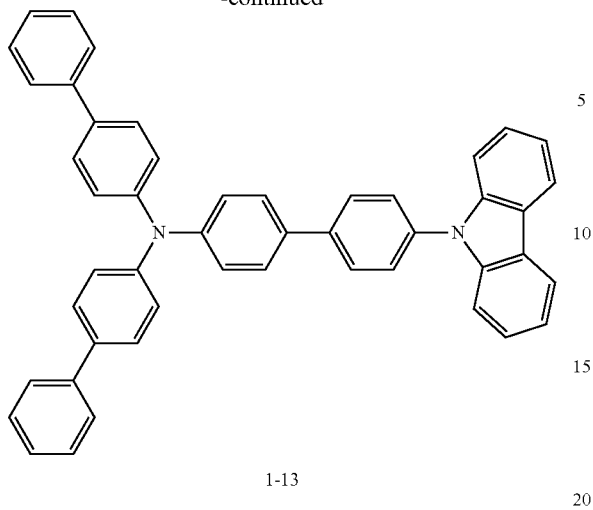

1-13

Compound represented by A' (46.6 mmol), Compound represented by B' (51.3 mmol), potassium carbonate (139.8 mmol) and tetrakis(triphenylphosphine)palladium(0) (0.9 mmol) were added to THF, and the mixture was refluxed for 18 hours. After the reaction was completed, the water layer was removed, the organic layer was dried with magnesium sulfate, and the filtrate was distilled under reduced pressure. The resulting solid was dissolved in chloroform (100 ml), and ethyl acetate (100 ml) was added thereto, followed by recrystallization and drying.

MS: [M+H]+=639

Preparation Example 2

1) Preparation of Compound 2-1

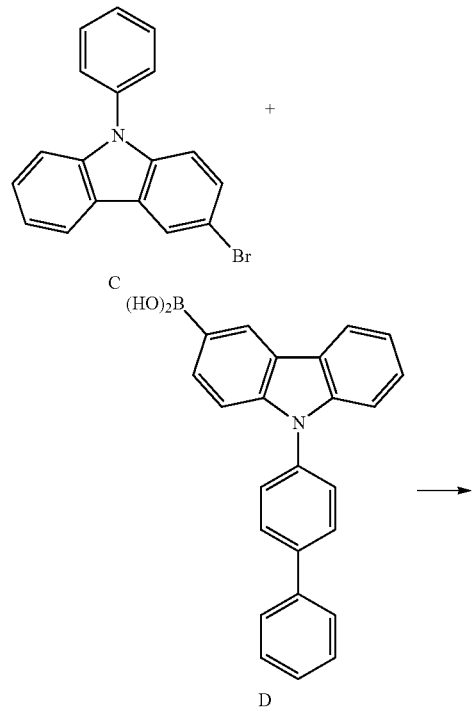

-continued

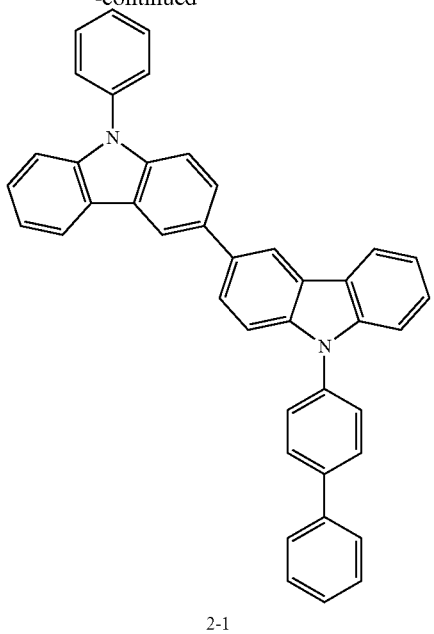

2-1

Compound represented by C (50 mmol), Compound represented by D (55 mmol), $K_2CO_3$ (100 mmol), and $Pd(PPh_3)_4$ were mixed with THF (200 mL) and $H_2O$ (100 mL), followed by stirring and refluxing for about 20 hours. After the reaction mixture was cooled down to room temperature, the water layer was removed and the organic layer was evaporated. The residue was dissolved in toluene and washed with water. After the water layer was removed, the organic layer was evaporated, and the residue was subjected to column chromatography using a silica gel.

MS: [M+H]+=561

Hereinafter, following compounds were prepared in the same manner as in the preparation of Compound 2-1, except that the Compound represented by C and the Compound represented by D were changed to correspond to the compound structure to be prepared.

2) Preparation of Compound 2-2

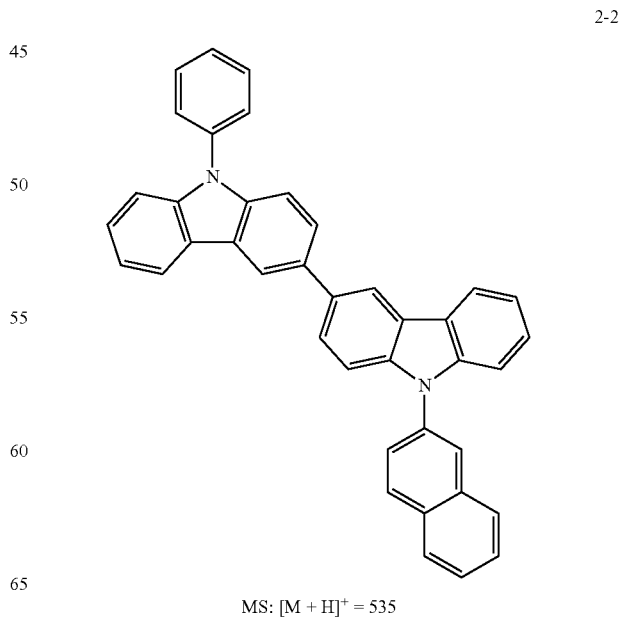

2-2

MS: $[M + H]^+ = 535$

3) Preparation of Compound 2-3
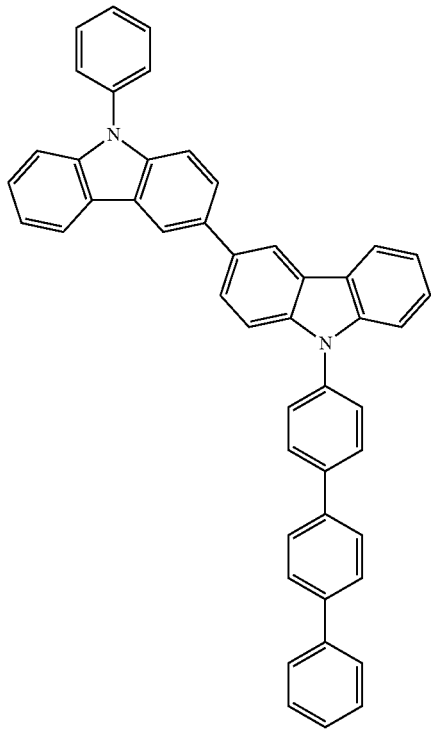
2-3
MS: [M + H]⁺ = 611
4) Preparation of Compound 2-4
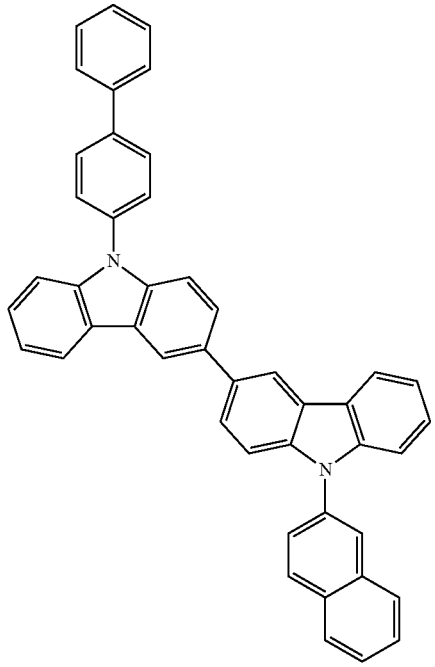
2-4
MS: [M + H]⁺ = 611
5) Preparation of Compound 2-5
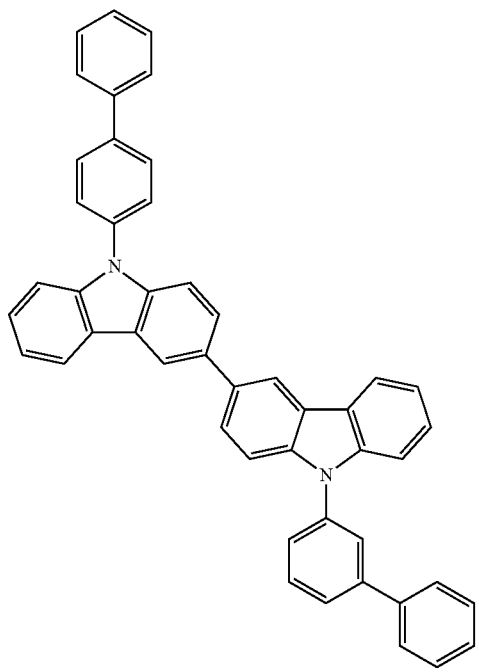
2-5
MS: [M + H]⁺ = 637
6) Preparation of Compound 2-10
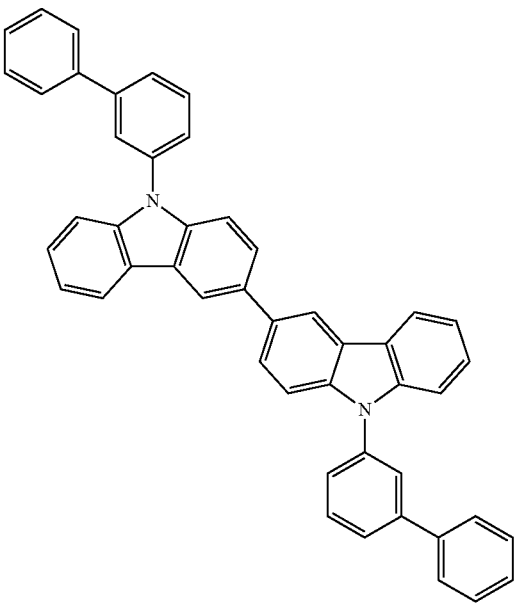
2-10
MS: [M + H]⁺ = 637

7) Preparation of Compound 2-11
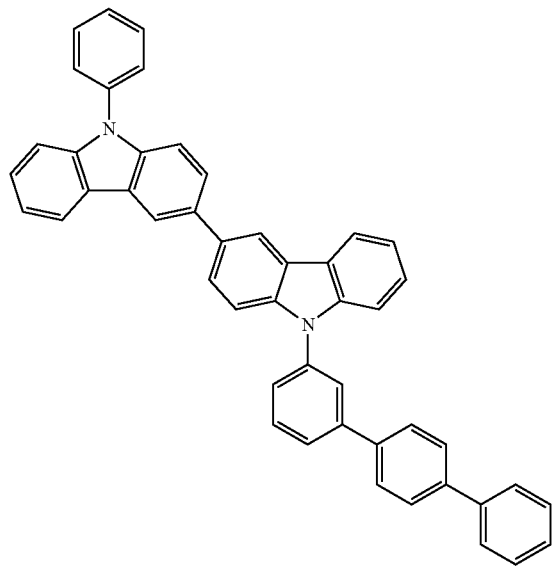
MS: [M + H]⁺ = 637
8) Preparation of Compound 2-12
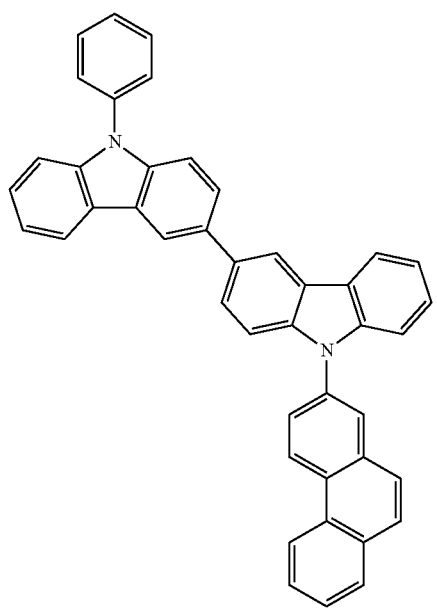
MS: [M + H]⁺ = 585
9) Preparation of Compound 2-13
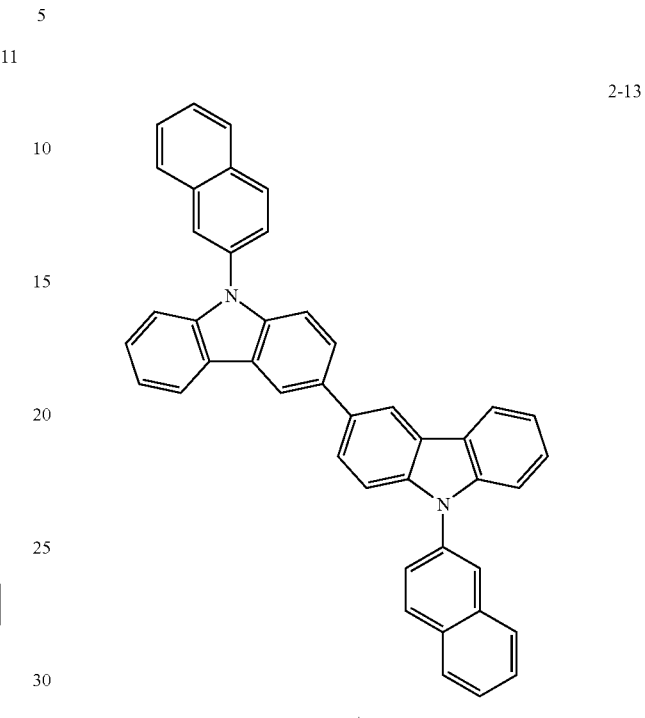
MS: [M+H]⁺ = 585
10) Preparation of Compound 2-23
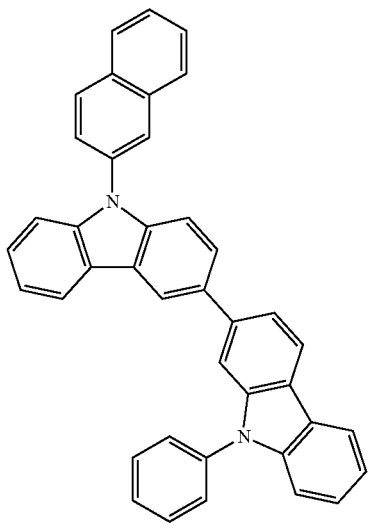
MS: [M+H]⁺ = 535

11) Preparation of the Compound 2-30

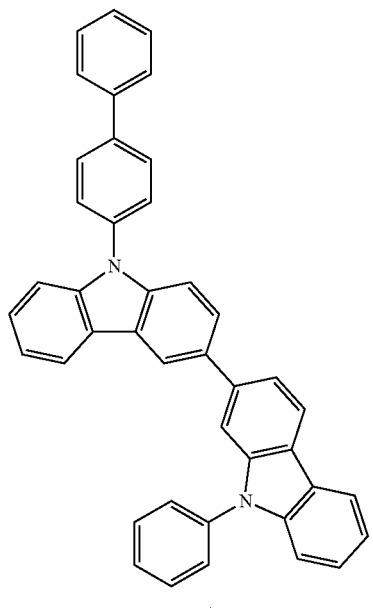

MS: [M+H]⁺ = 561

Preparation Example 3

1) Preparation of the Compound 3-1

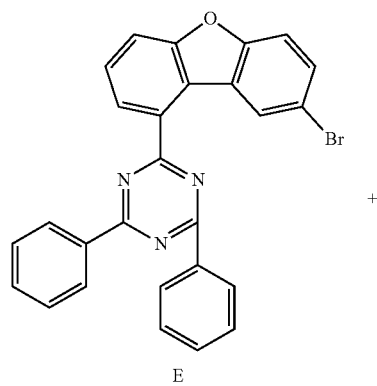

E

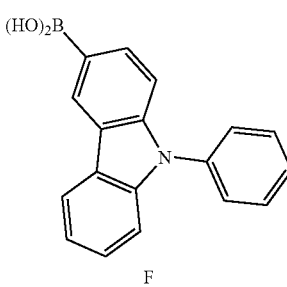

F

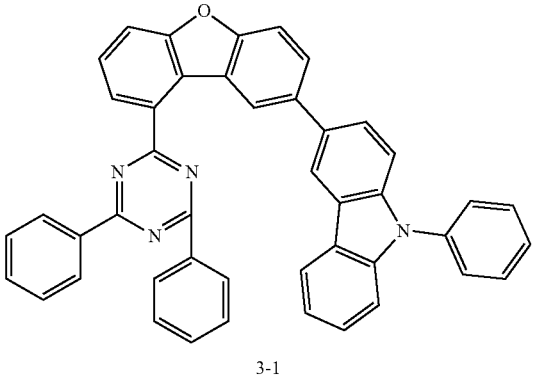

3-1

Compound represented by E (156 mmol), Compound represented by F (172 mmol), sodium carbonate (340 mmol) were mixed with ethylene glycol diamine ether (1000 mL) and water (280 mL). Tetrakis(triphenylphosphine)palladium (0) (1.5 mmol) was added herein, and the mixture was heated under reflux for 16 hours. After the reaction mixture was cooled down to room temperature, the organic phase was separated, filtered through a silica gel, washed three times with 200 mL of water, and subsequently evaporated. The product was purified using a column chromatography on a silica gel with toluene/heptane (1:2) and sublimed under vacuum.

MS: [M+H]+=641

2) Preparation of Compound 3-2

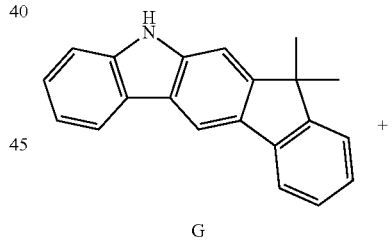

G

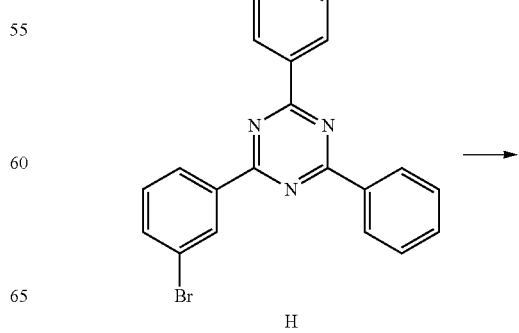

H

-continued

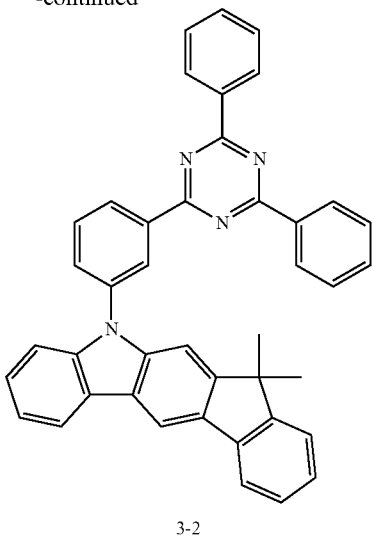

3-2

Compound represented by G (67 mmol), Compound represented by H (74 mmol), and 19.3 g of NaOtBu were mixed with 1000 mL of p-xylene. And then Pd(OAc)$_2$ (1.34 mmol) and 1 M tri-tert-butylphosphine solution (1 mL) were added to the suspension. The reaction mixture was heated under reflux for 16 hours. After the reaction mixture was cooled down to room temperature, dichloromethane was added thereto, the organic phase was separated, washed three times with 200 mL of water, and then evaporated. The residue was extracted with hot toluene, recrystallized from toluene and finally sublimed under vacuum.

MS: [M+H]+=591

Example 1

The glass substrate on which a thin film of ITO (indium tin oxide) was applied in a thickness of 150 nm was put into distilled water having the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was finished, washing with ultrasonic waves was performed using solvents of isopropyl alcohol, acetone, and methanol. And then the glass substrate was dried, and transported to a plasma scrubber. The substrate was washed using oxygen plasma for 5 minutes, and transported to a vacuum evaporator. And then a following HI-1 compound was thermally deposited under vacuum to a thickness of 50 nm on the ITO transparent electrode prepared above to form a hole injection layer.

And the Compound prepared in Preparation Example 1-1 was thermally deposited under vacuum to form a hole transport layer in a thickness of 100 nm. And then the Compounds prepared in Preparation Example 1-1 and 2-1 (a weight ratio of 7:3) as hosts and a following RD compound (2 wt % based on the host) as a dopant were simultaneously deposited under vacuum to form a first light emitting layer in a thickness of 150 nm. The Compounds prepared in Preparation Example 2-1 and 3-2 (a weight ratio of 3:7) as hosts and a following YGD compound (10 wt % based on the hosts) as a dopant were simultaneously deposited under vacuum to form a second light emitting layer in a thickness of 300 nm. And then the Compounds prepared in Preparation Example 2-1 and 3-2 (a weight ratio of 3:7) as hosts and a following GD compound (5 wt % based on the host) as a dopant were simultaneously deposited under vacuum to form a third light emitting layer in a thickness of 100 nm.

And a following ET2 compound was deposited under vacuum to form an electron transport layer in a thickness of 250 nm. And then a following ET1 compound (lithium doping amount of 2%) was deposited under vacuum to form an electron injection layer in a thickness of 100 nm. And aluminum was deposited to form a cathode, thereby preparing an organic light emitting device.

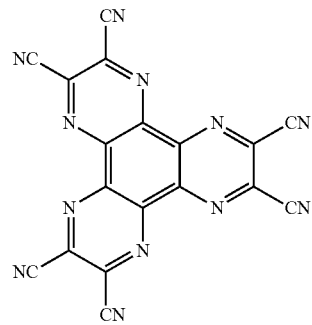

HI-1

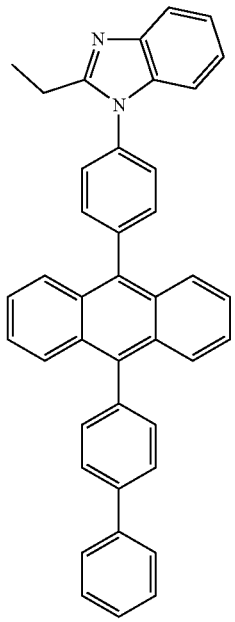

ET-2

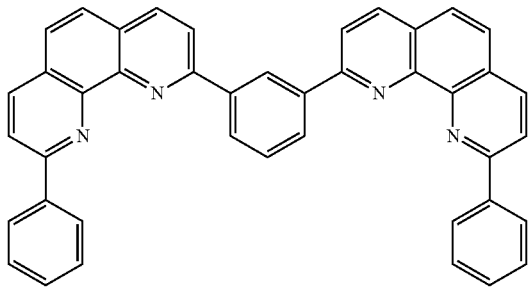

ET-1

-continued

RD
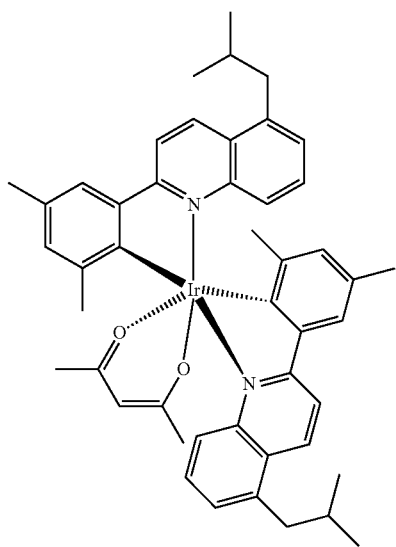

-continued

GD
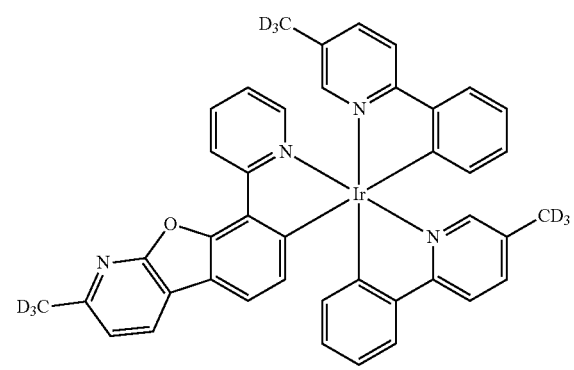

Examples 2 to 23 and Comparative Examples 1 to 8

An organic light emitting device was prepared in the same manner as in Example 1, except that Compounds described in Table 1 and Table 2 below were used as the hole transport layer, the first light emitting layer, the second light emitting layer, and the third light emitting layer. In Table 1 and Table 2, each material means the number of the Preparation Example and the value in parentheses means weight %.

Meanwhile, RH in Table 2 means that a following compound was used.

RH
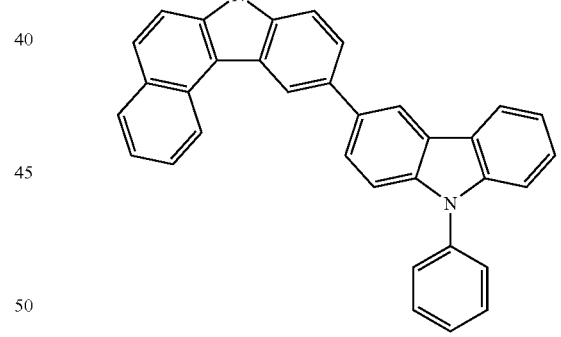

YGD
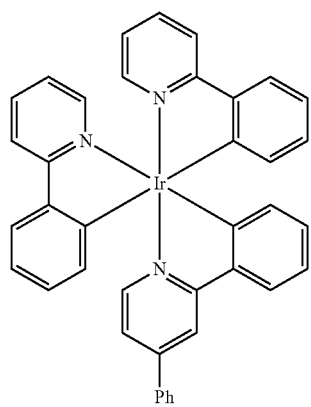

TABLE 1

|  | HTL | Red Host | | YG Host | | Green Host | |
|---|---|---|---|---|---|---|---|
| Example 1 | 1-1 | 1-1 (70%) | 2-1 (30%) | 2-1 (30%) | 3-2 (70%) | 2-1 (30%) | 3-2 (70%) |
| Example 2 | 1-7 | 1-7 (70%) | 2-1 (30%) | 2-1 (30%) | 3-2 (70%) | 2-1 (30%) | 3-2 (70%) |
| Example 3 | 1-8 | 1-8 (70%) | 2-1 (30%) | 2-1 (30%) | 3-2 (70%) | 2-1 (30%) | 3-2 (70%) |
| Example 4 | 1-13 | 1-13 (70%) | 2-1 (30%) | 2-1 (30%) | 3-2 (70%) | 2-1 (30%) | 3-2 (70%) |
| Example 5 | 1-13 | 1-13 (50%) | 2-1 (50%) | 2-1 (30%) | 3-2 (70%) | 2-1 (30%) | 3-2 (70%) |
| Example 6 | 1-13 | 1-13 (30%) | 2-1 (70%) | 2-1 (30%) | 3-2 (70%) | 2-1 (30%) | 3-2 (70%) |
| Example 7 | 1-13 | 1-13 (70%) | 2-1 (30%) | 2-1 (50%) | 3-2 (70%) | 2-1 (30%) | 3-2 (70%) |
| Example 8 | 1-13 | 1-13 (70%) | 2-1 (30%) | 2-1 (70%) | 3-2 (70%) | 2-1 (30%) | 3-2 (70%) |
| Example 9 | 1-13 | 1-13 (70%) | 2-1 (30%) | 2-1 (30%) | 3-2 (70%) | 2-1 (50%) | 3-2 (50%) |
| Example 10 | 1-13 | 1-13 (70%) | 2-1 (30%) | 2-1 (30%) | 3-2 (70%) | 2-1 (70%) | 3-2 (30%) |
| Example 11 | 1-1 | 1-1 (70%) | 2-2 (30%) | 2-2 (30%) | 3-2 (70%) | 2-2 (30%) | 3-2 (70%) |
| Example 12 | 1-7 | 1-7 (70%) | 2-3 (30%) | 2-3 (30%) | 3-2 (70%) | 2-3 (30%) | 3-2 (70%) |

TABLE 1-continued

|  | HTL | Red Host | | YG Host | | Green Host | |
|---|---|---|---|---|---|---|---|
| Example 13 | 1-13 | 1-13 (70%) | 2-4 (30%) | 2-4 (30%) | 3-2 (70%) | 2-4 (30%) | 3-2 (70%) |
| Example 14 | 1-1 | 1-1 (70%) | 2-5 (30%) | 2-5 (30%) | 3-2 (70%) | 2-5 (30%) | 3-2 (70%) |
| Example 15 | 1-7 | 1-7 (70%) | 2-10 (30%) | 2-10 (30%) | 3-2 (70%) | 2-10 (30%) | 3-2 (70%) |
| Example 16 | 1-13 | 1-13 (70%) | 2-11 (30%) | 2-11 (30%) | 3-2 (70%) | 2-11 (30%) | 3-2 (70%) |
| Example 17 | 1-1 | 1-1 (70%) | 2-12 (30%) | 2-12 (30%) | 3-2 (70%) | 2-12 (30%) | 3-2 (70%) |
| Example 18 | 1-7 | 1-7 (70%) | 2-13 (30%) | 2-13 (30%) | 3-2 (70%) | 2-13 (30%) | 3-2 (70%) |
| Example 19 | 1-13 | 1-13 (70%) | 2-23 (30%) | 2-23 (30%) | 3-2 (70%) | 2-23 (30%) | 3-2 (70%) |
| Example 20 | 1-1 | 1-1 (70%) | 2-30 (30%) | 2-30 (30%) | 3-2 (70%) | 2-30 (30%) | 3-2 (70%) |
| Example 21 | 1-1 | 1-1 (70%) | 2-1 (30%) | 2-1 (30%) | 3-1 (70%) | 2-1 (30%) | 3-1 (70%) |
| Example 22 | 1-7 | 1-7 (70%) | 2-1 (30%) | 2-1 (30%) | 3-1 (70%) | 2-1 (30%) | 3-2 (70%) |
| Example 23 | 1-13 | 1-13 (70%) | 2-1 (30%) | 2-1 (30%) | 3-2 (70%) | 2-1 (30%) | 3-1 (70%) |

TABLE 2

|  | HTL | Red Host | | YG Host | | Green Host | |
|---|---|---|---|---|---|---|---|
| Comparative Example 1 | 1-1 | RH (100%) | | 3-1 (100%) | | 3-2 (100%) | |
| Comparative Example 2 | 1-7 | RH (50%) | 2-1 (50%) | 2-1 (30%) | 3-1 (70%) | 2-1 (30%) | 3-2 (70%) |
| Comparative Example 3 | 1-8 | RH (50%) | 2-1 (50%) | 2-1 (30%) | 3-2 (70%) | 2-1 (30%) | 3-1 (70%) |
| Comparative Example 4 | 1-13 | RH (50%) | 2-2 (50%) | 2-4 (30%) | 3-1 (70%) | 2-4 (30%) | 3-1 (70%) |
| Comparative Example 5 | 1-1 | 1-1 (70%) | 2-5 (30%) | 2-30 (30%) | 3-1 (70%) | 2-30 (30%) | 3-1 (70%) |
| Comparative Example 6 | 1-7 | 1-7 (70%) | 2-12 (30%) | 2-5 (30%) | 3-2 (70%) | 2-5 (30%) | 3-2 (70%) |
| Comparative Example 7 | 1-8 | 1-8 (70%) | 2-5 (30%) | 2-10 (30%) | 3-1 (70%) | 2-10 (30%) | 3-1 (70%) |
| Comparative Example 8 | 1-13 | 1-13 (70%) | 2-11 (30%) | 2-23 (30%) | 3-2 (70%) | 2-23 (30%) | 3-2 (70%) |

Experimental Example 1

Currents were applied to the organic light emitting devices prepared in Examples 1 to 23 and Comparative Examples 1 to 8 to obtain the results shown in Table 3 and Table 4 below.

TABLE 3

|  | @10 mA/cm$^2$ | | | | @100 mA/cm$^2$ |
|---|---|---|---|---|---|
|  | V | Cd/A | CIE_x | CIE_y | LT (95%) hours |
| Example 1 | 5.72 | 61.87 | 0.428 | 0.557 | 177 |
| Example 2 | 5.21 | 60.02 | 0.447 | 0.540 | 163 |
| Example 3 | 4.84 | 60.27 | 0.469 | 0.520 | 187 |
| Example 4 | 5.01 | 56.12 | 0.481 | 0.509 | 152 |
| Example 5 | 5.22 | 58.04 | 0.487 | 0.503 | 160 |
| Example 6 | 4.94 | 55.32 | 0.491 | 0.503 | 147 |
| Example 7 | 5.37 | 59.36 | 0.494 | 0.500 | 175 |
| Example 8 | 5.52 | 60.18 | 0.469 | 0.497 | 179 |
| Example 9 | 4.84 | 60.27 | 0.443 | 0.520 | 165 |
| Example 10 | 4.44 | 66.98 | 0.467 | 0.543 | 166 |
| Example 11 | 5.00 | 68.73 | 0.440 | 0.523 | 146 |
| Example 12 | 4.60 | 72.81 | 0.487 | 0.546 | 170 |
| Example 13 | 5.13 | 54.22 | 0.477 | 0.503 | 164 |
| Example 14 | 5.15 | 61.62 | 0.482 | 0.514 | 148 |
| Example 15 | 5.13 | 56.44 | 0.486 | 0.508 | 149 |
| Example 16 | 4.89 | 56.46 | 0.476 | 0.504 | 152 |
| Example 17 | 5.18 | 55.45 | 0.486 | 0.514 | 168 |
| Example 18 | 5.05 | 59.82 | 0.481 | 0.505 | 172 |
| Example 19 | 5.02 | 56.12 | 0.487 | 0.509 | 159 |
| Example 20 | 5.21 | 52.54 | 0.478 | 0.503 | 157 |
| Example 21 | 5.17 | 58.53 | 0.478 | 0.512 | 177 |
| Example 22 | 4.89 | 56.48 | 0.478 | 0.512 | 143 |
| Example 23 | 3.66 | 63.47 | 0.490 | 0.503 | 173 |

TABLE 4

|  | @10 mA/cm$^2$ | | | | @100 mA/cm$^2$ |
|---|---|---|---|---|---|
|  | V | Cd/A | CIE_x | CIE_y | LT (95%) hours |
| Comparative Example 1 | 5.72 | 38.59 | 0.513 | 0.479 | 121 |
| Comparative Example 2 | 5.72 | 37.89 | 0.517 | 0.475 | 109 |
| Comparative Example 3 | 5.92 | 36.57 | 0.521 | 0.475 | 87 |
| Comparative Example 4 | 5.88 | 35.78 | 0.524 | 0.469 | 93 |
| Comparative Example 5 | 5.79 | 36.45 | 0.520 | 0.472 | 108 |
| Comparative Example 6 | 6.12 | 35.51 | 0.524 | 0.468 | 127 |
| Comparative Example 7 | 6.03 | 37.28 | 0.519 | 0.473 | 114 |
| Comparative Example 8 | 5.87 | 37.70 | 0.514 | 0.478 | 76 |

Example 24

The glass substrate on which a thin film of ITO (indium tin oxide) was applied in a thickness of 150 nm was put into distilled water having the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was finished, washing with ultrasonic waves was performed using solvents of isopropyl alcohol, acetone, and methanol. And then the glass substrate was dried, and transported to a plasma scrubber. The substrate was washed using oxygen plasma for 5 minutes, and then transported to a vacuum evaporator. The HI-1 compound was thermally deposited under vacuum to a thickness of 50 nm on the ITO transparent electrode prepared above to form a hole injection layer.

And the Compound prepared in Preparation Example 1-1 was thermally deposited under vacuum to form a hole transport layer in a thickness of 100 nm. And then the Compounds prepared in Preparation Example 1-1 and 2-1 (a weight ratio of 7:3) as hosts and the RD compound (2 wt % based on the host) as a dopant were simultaneously deposited under vacuum to form a first light emitting layer in a thickness of 100 nm. The Compounds prepared in Preparation Example 2-1 and 3-2 (a weight ratio of 3:7) as hosts and the YGD compound (10 wt % based on the hosts) as a dopant were simultaneously deposited under vacuum to form a second light emitting layer in a thickness of 400 nm.

And the ET2 compound was deposited under vacuum to form an electron transport layer in a thickness of 250 nm. And then the ET1 compound (lithium doping amount of 2%) was deposited under vacuum to form an electron injection layer in a thickness of 100 nm. And aluminum was deposited to form a cathode, thereby preparing an organic light emitting device.

Examples 25 to 43 and Comparative Examples 9 to 16

An organic light emitting device was prepared in the same manner as in Example 24, except that Compounds described in Table 5 and Table 6 below were used as the hole transport layer, the first light emitting layer, and the second light emitting layer. In Table 5 and Table 6, each material means the number of the Preparation Example and the value in parentheses means weight %.

TABLE 5

| | HTL | Red Host | | YG Host | |
|---|---|---|---|---|---|
| Example 24 | 1-1 | 1-1 (70%) | 2-1 (30%) | 2-1 (30%) | 3-2 (70%) |
| Example 25 | 1-7 | 1-7 (70%) | 2-1 (30%) | 2-1 (30%) | 3-2 (70%) |
| Example 26 | 1-8 | 1-8 (70%) | 2-1 (30%) | 2-1 (30%) | 3-2 (70%) |
| Example 27 | 1-13 | 1-13 (70%) | 2-1 (30%) | 2-1 (30%) | 3-2 (70%) |
| Example 28 | 1-13 | 1-13 (50%) | 2-1 (50%) | 2-1 (30%) | 3-2 (70%) |
| Example 29 | 1-13 | 1-13 (30%) | 2-1 (70%) | 2-1 (30%) | 3-2 (70%) |
| Example 30 | 1-13 | 1-13 (70%) | 2-1 (30%) | 2-1 (50%) | 3-2 (50%) |
| Example 31 | 1-13 | 1-13 (70%) | 2-1 (30%) | 2-1 (70%) | 3-2 (30%) |
| Example 32 | 1-1 | 1-1 (70%) | 2-2 (30%) | 2-2 (30%) | 3-1 (70%) |
| Example 33 | 1-7 | 1-7 (70%) | 2-3 (30%) | 2-3 (30%) | 3-1 (70%) |
| Example 34 | 1-13 | 1-13 (70%) | 2-4 (30%) | 2-4 (30%) | 3-1 (70%) |
| Example 35 | 1-1 | 1-1 (70%) | 2-5 (30%) | 2-5 (30%) | 3-1 (70%) |
| Example 36 | 1-7 | 1-7 (70%) | 2-10 (30%) | 2-10 (30%) | 3-1 (70%) |
| Example 37 | 1-13 | 1-13 (70%) | 2-11 (30%) | 2-11 (30%) | 3-1 (70%) |
| Example 38 | 1-1 | 1-1 (70%) | 2-12 (30%) | 2-12 (30%) | 3-2 (70%) |
| Example 39 | 1-7 | 1-7 (70%) | 2-13 (30%) | 2-13 (30%) | 3-1 (70%) |
| Example 40 | 1-13 | 1-13 (70%) | 2-23 (30%) | 2-23 (30%) | 3-2 (70%) |
| Example 41 | 1-1 | 1-1 (70%) | 2-30 (30%) | 2-30 (30%) | 3-1 (70%) |
| Example 42 | 1-7 | 1-7 (70%) | 2-1 (30%) | 2-1 (30%) | 3-1 (70%) |
| Example 43 | 1-13 | 1-13 (70%) | 2-1 (30%) | 2-1 (30%) | 3-1 (70%) |

TABLE 6

| | HTL | Red Host | | YG Host | |
|---|---|---|---|---|---|
| Comparative Example 9 | 1-1 | RH (100%) | | 3-1 (100%) | |
| Comparative Example 10 | 1-7 | RH (50%) | 2-30 (50%) | 2-30 (30%) | 3-1 (70%) |
| Comparative Example 11 | 1-8 | RH (50%) | 2-23 (50%) | 2-13 (30%) | 3-2 (70%) |
| Comparative Example 12 | 1-13 | RH (50%) | 2-11 (50%) | 2-12 (30%) | 3-1 (70%) |
| Comparative Example 13 | 1-1 | 1-1 (70%) | 2-5 (30%) | 2-10 (30%) | 3-1 (70%) |
| Comparative Example 14 | 1-7 | 1-7 (70%) | 2-4 (30%) | 2-4 (30%) | 3-2 (70%) |
| Comparative Example 15 | 1-8 | 1-8 (70%) | 2-1 (30%) | 2-13 (30%) | 3-1 (70%) |
| Comparative Example 16 | 1-13 | 1-13 (70%) | 2-2 (30%) | 2-23 (30%) | 3-2 (70%) |

Experimental Example 2

Currents were applied to the organic light emitting devices prepared in Examples 24 to 43 and Comparative Examples 9 to 16 to obtain the results shown in Table 7 and Table 8 below.

TABLE 7

|  | @10 mA/cm² | | | | @100 mA/cm² |
| --- | --- | --- | --- | --- | --- |
|  | V | Cd/A | CIE_x | CIE_y | LT (95%) hours |
| Example 24 | 3.92 | 56.28 | 0.497 | 0.496 | 125 |
| Example 25 | 3.80 | 58.79 | 0.493 | 0.500 | 127 |
| Example 26 | 3.94 | 59.70 | 0.499 | 0.494 | 132 |
| Example 27 | 4.03 | 57.65 | 0.498 | 0.495 | 119 |
| Example 28 | 3.90 | 60.56 | 0.495 | 0.499 | 121 |
| Example 29 | 3.98 | 60.94 | 0.497 | 0.496 | 110 |
| Example 30 | 3.92 | 65.37 | 0.495 | 0.498 | 134 |
| Example 31 | 4.15 | 65.38 | 0.500 | 0.493 | 132 |
| Example 32 | 4.04 | 66.11 | 0.496 | 0.497 | 147 |
| Example 33 | 3.91 | 61.76 | 0.495 | 0.498 | 137 |
| Example 34 | 3.93 | 61.03 | 0.498 | 0.496 | 132 |
| Example 35 | 4.05 | 60.10 | 0.500 | 0.494 | 140 |
| Example 36 | 4.05 | 57.41 | 0.501 | 0.492 | 119 |
| Example 37 | 3.92 | 59.38 | 0.498 | 0.495 | 125 |
| Example 38 | 3.98 | 56.63 | 0.500 | 0.493 | 138 |
| Example 39 | 4.15 | 63.31 | 0.502 | 0.491 | 141 |
| Example 40 | 4.09 | 64.69 | 0.500 | 0.493 | 123 |
| Example 41 | 3.99 | 60.82 | 0.499 | 0.494 | 128 |
| Example 42 | 3.99 | 59.15 | 0.498 | 0.495 | 132 |
| Example 43 | 4.02 | 58.45 | 0.499 | 0.494 | 132 |

TABLE 8

|  | @10 mA/cm² | | | | @100 mA/cm² |
| --- | --- | --- | --- | --- | --- |
|  | V | Cd/A | CIE_x | CIE_y | LT (95%) hours |
| Comparative Example 9 | 4.02 | 40.56 | 0.493 | 0.499 | 72 |
| Comparative Example 10 | 4.02 | 38.19 | 0.493 | 0.499 | 77 |
| Comparative Example 11 | 4.03 | 36.97 | 0.494 | 0.499 | 53 |
| Comparative Example 12 | 4.03 | 35.83 | 0.496 | 0.496 | 65 |
| Comparative Example 13 | 4.05 | 37.99 | 0.526 | 0.468 | 21 |
| Comparative Example 14 | 4.01 | 39.17 | 0.507 | 0.486 | 76 |
| Comparative Example 15 | 4.03 | 45.89 | 0.513 | 0.481 | 80 |
| Comparative Example 16 | 4.04 | 45.49 | 0.521 | 0.472 | 55 |

DESCRIPTION OF SYMBOLS

1: substrate
2: anode
3: hole transport layer
4: first light emitting layer
5: second light emitting layer
6: electron transport layer
7: cathode
8: anode

The invention claimed is:

1. An organic light emitting device comprising:
a first electrode;
a hole transport layer;
a first light emitting layer;
a second light emitting layer;
a third light emitting layer;
an electron transport layer; and
a second electrode,
wherein the first light emitting layer comprises a 1-1 host and a 1-2 host,
the second light emitting layer comprises a 2-1 host and a 2-2 host,
the hole transport layer comprises the same material as the 1-1 host,
the 1-1 host and the 2-2 host are different materials from each other,
wherein the third light emitting layer is disposed between the second light emitting layer and the electron transport layer, and comprises a 3-1 host and a 3-2 host,
the 1-2 host, the 2-1 host and the 3-1 host are the same materials, and
wherein the 1-2 host is a compound represented by Chemical Formula 2:

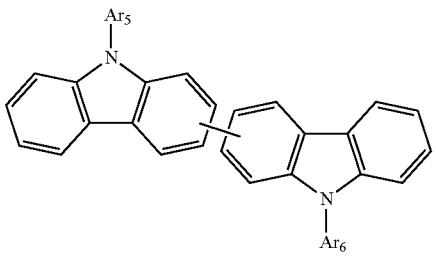

[Chemical Formula 2]

in Chemical Formula 2,
$Ar_5$ and $Ar_6$ are each independently a substituted or unsubstituted $C_{6-60}$ aryl.

2. The organic light emitting device of claim 1,
wherein the 1-1 host is a compound represented by Chemical Formula 1:

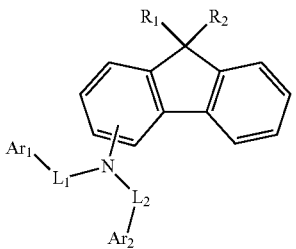

[Chemical Formula 1]

in Chemical Formula 1,
$R_1$ and $R_2$ are each independently hydrogen; deuterium; halogen; nitrile; nitro; amino; a substituted or unsubstituted $C_1$-60 alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heterocyclic group containing at least one of O, N, Si and S,
$L_1$ and $L_2$ are each independently a bond, or a substituted or unsubstituted $C_{6-60}$ arylene, and
$Ar_1$ and $Ar_2$ are each independently a substituted or unsubstituted $C_{6-60}$ aryl; or a substituted or unsubstituted $C_2$-60 heteroaryl containing at least one of O, N, Si and S.

3. The organic light emitting device of claim 2, wherein the compound represented by the Chemical Formula 1 is any one selected from the group consisting of:
1-1
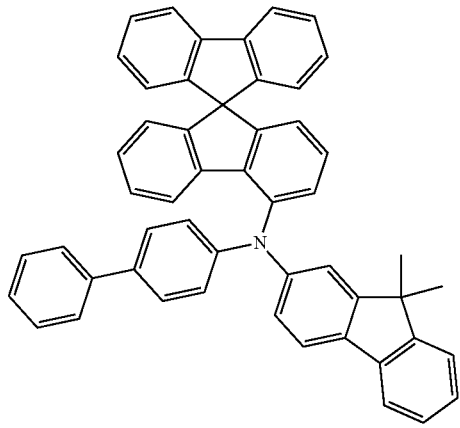
1-2
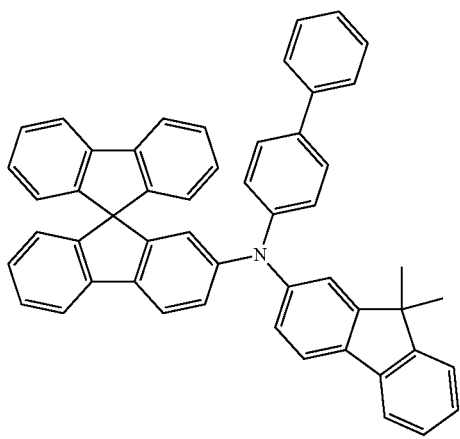
1-3
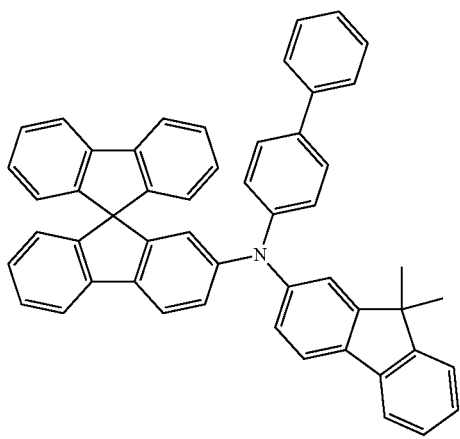
-continued
1-4
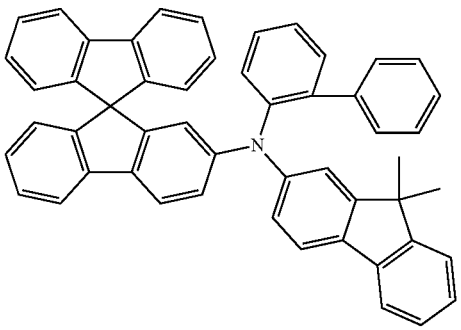
1-5
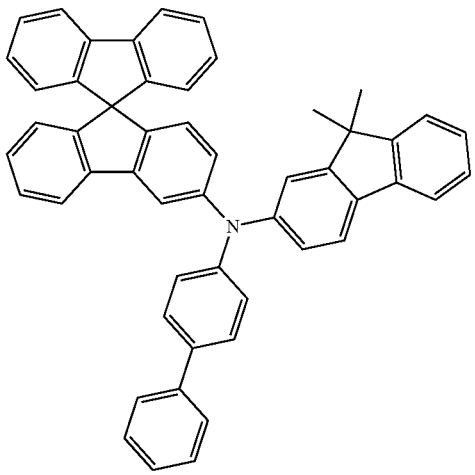
1-6
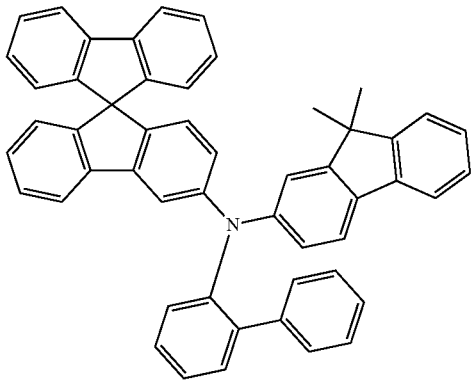
1-7
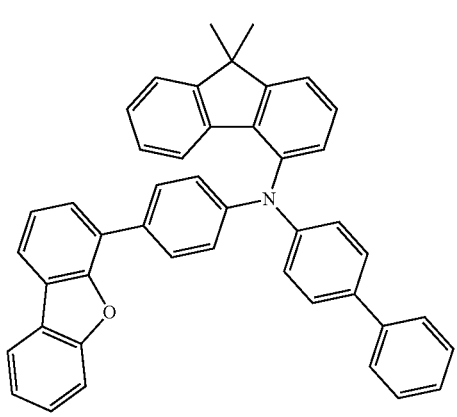

1-8
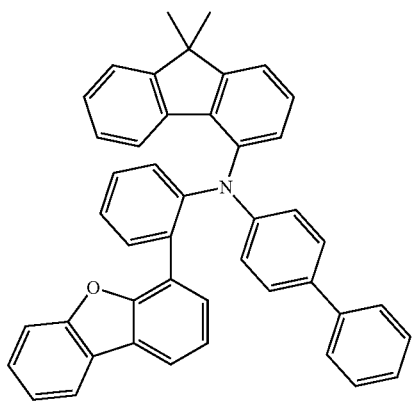

1-9
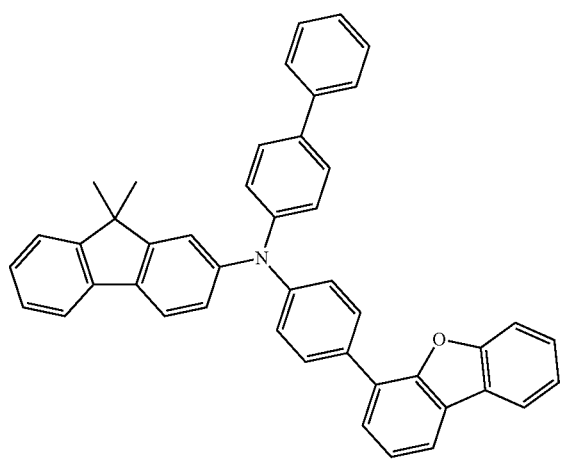

1-10
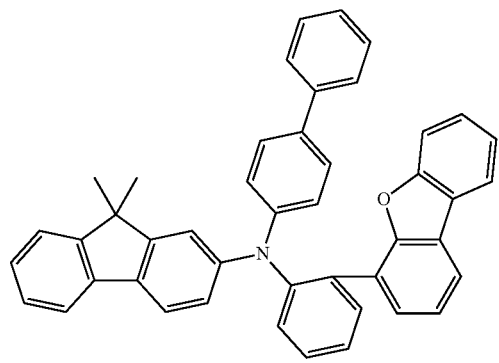

1-11
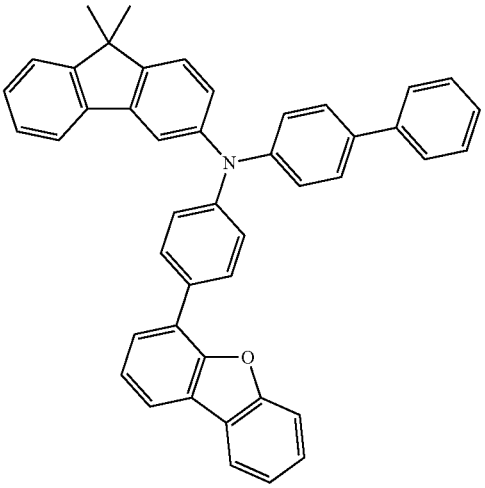

1-12
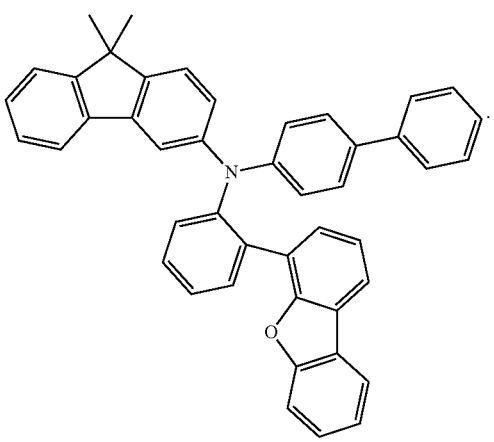

4. The organic light emitting device of claim 1, wherein the 1-1 host is a compound represented by Chemical Formula 1':

[Chemical Formula 1']

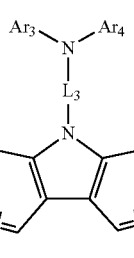

in Chemical Formula 1', $R_3$ and $R_4$ are each independently hydrogen; deuterium; halogen; nitrile; nitro; amino; a substituted or unsubstituted $C_1$-60 alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted C$_{2-60}$ heterocyclic group containing at least one of O, N, Si and S, L$_3$ is a bond, or a substituted or unsubstituted C$_6$-60 arylene, and Ar$_3$ and Ar$_4$ are each independently a substituted or unsubstituted C$_{6-60}$ aryl; or a substituted or unsubstituted C$_2$-60 heteroaryl containing at least one of O, N, Si and S.

5. The organic light emitting device of claim 4,
wherein the compound represented by the Chemical Formula 1' is a following compound:

1-13

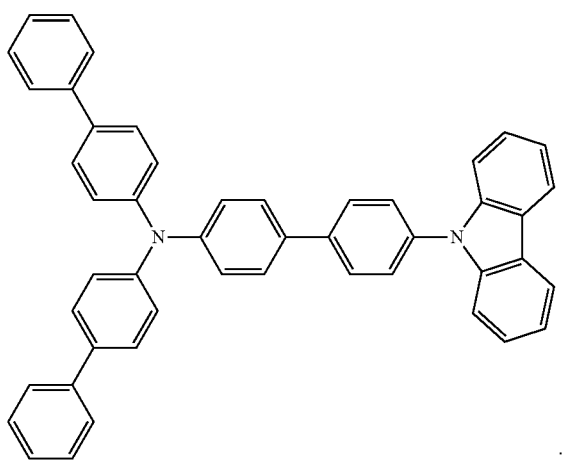

6. The organic light emitting device of claim 1,
wherein the compound represented by the Chemical Formula 2 is any one selected from the group consisting of:

2-1

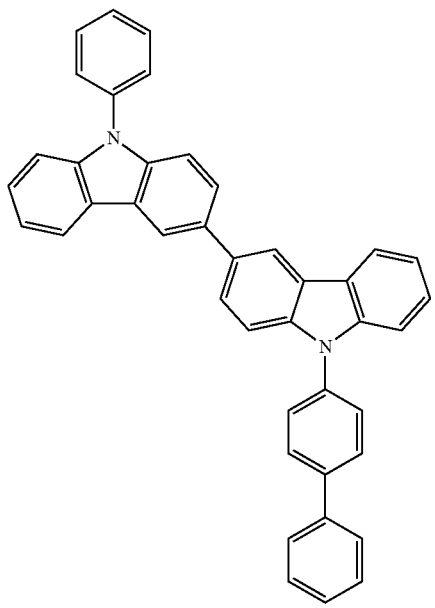

2-2

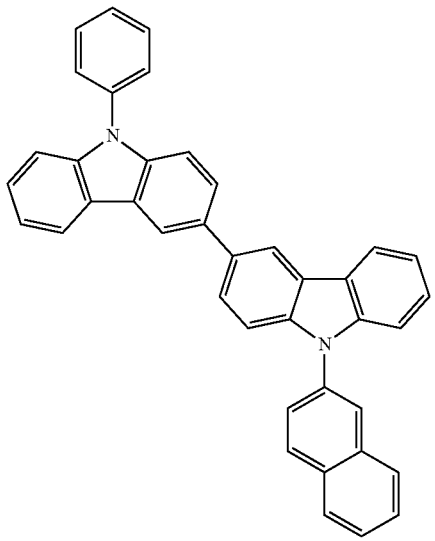

-continued 2-3

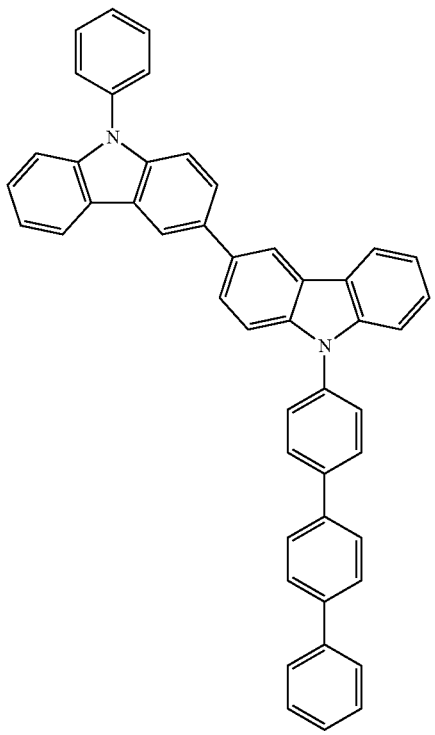

2-4
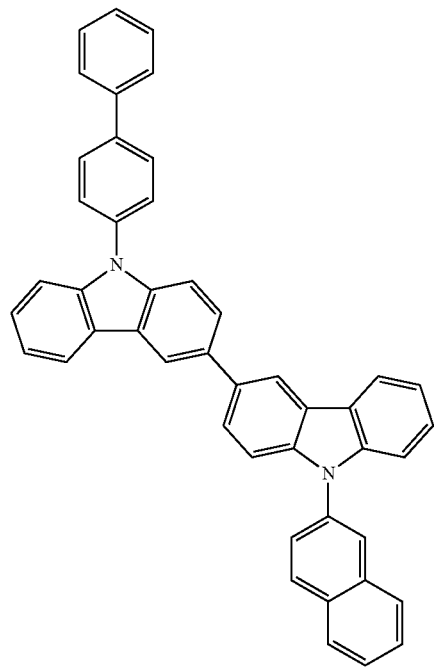
2-5
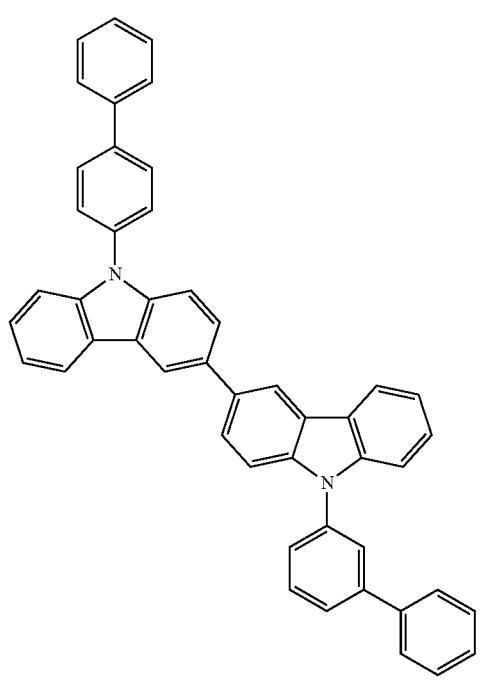
2-6
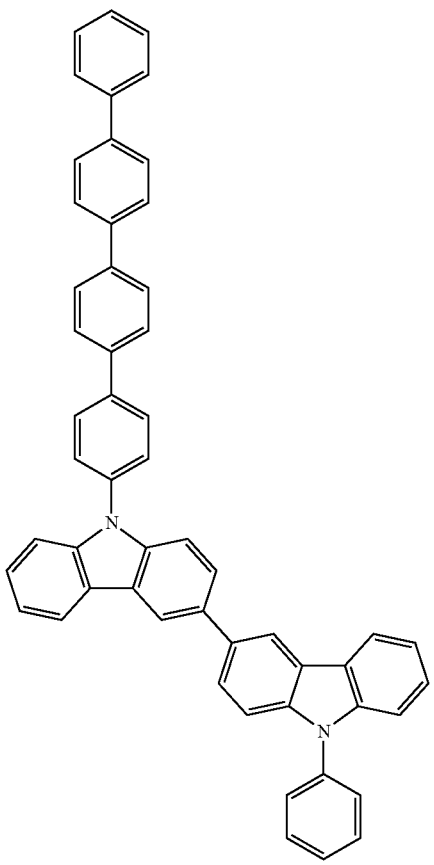
2-7
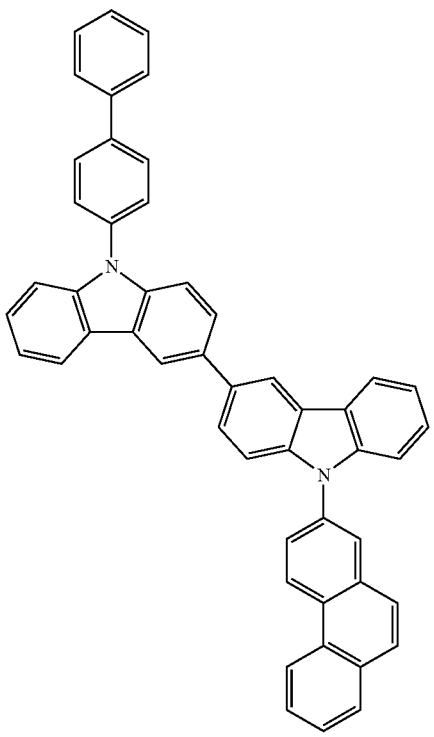

2-8
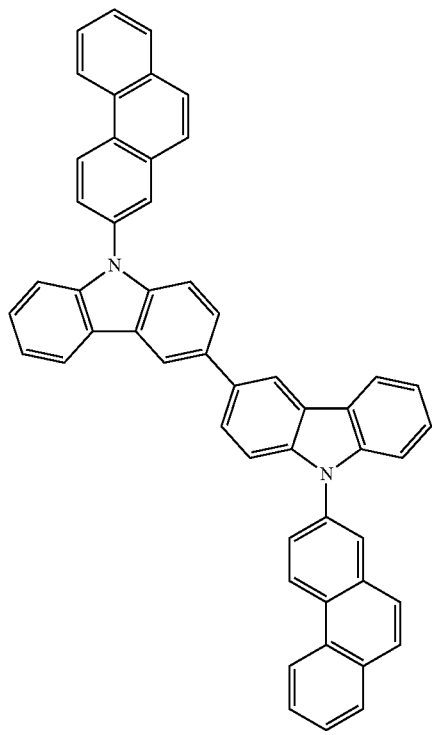
2-9
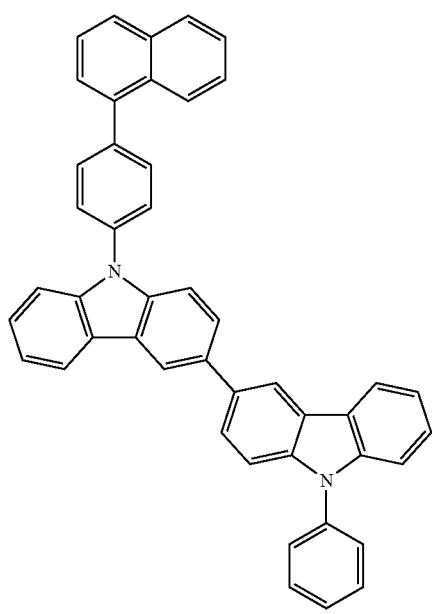
2-10
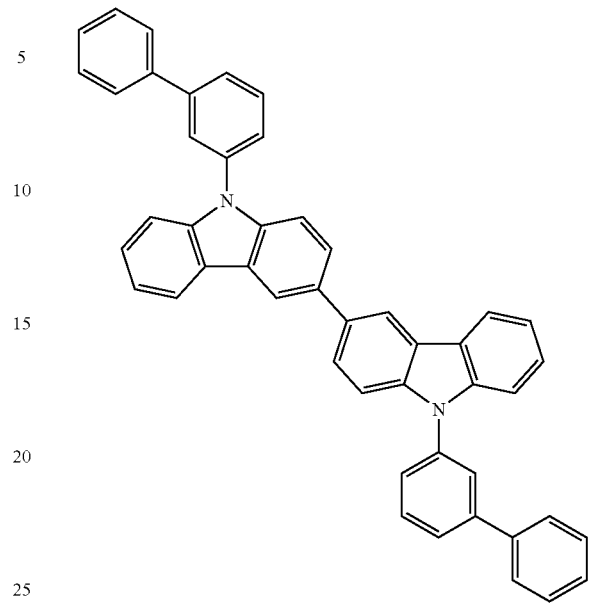
2-11
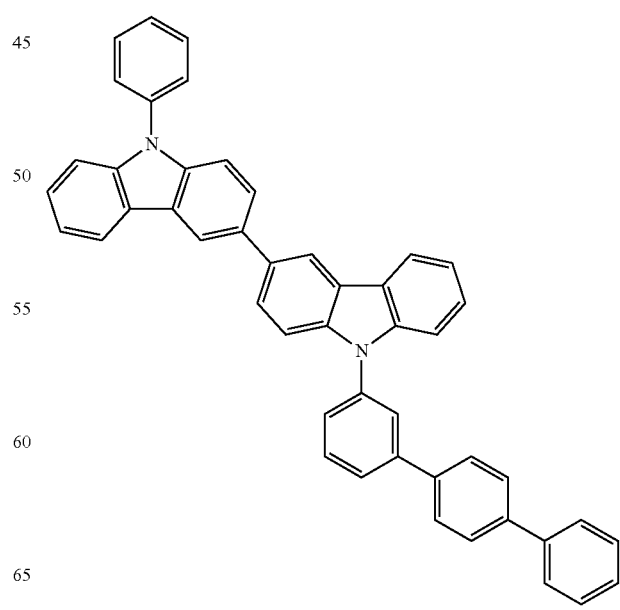

-continued
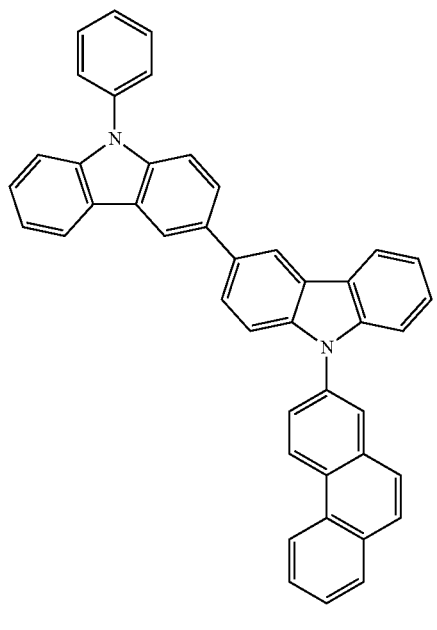
2-12
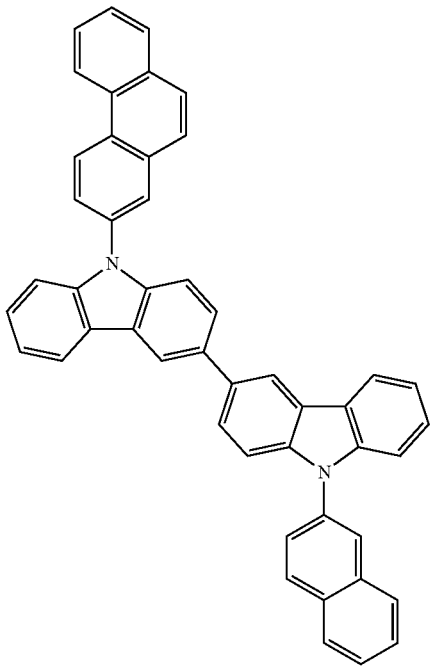
2-14
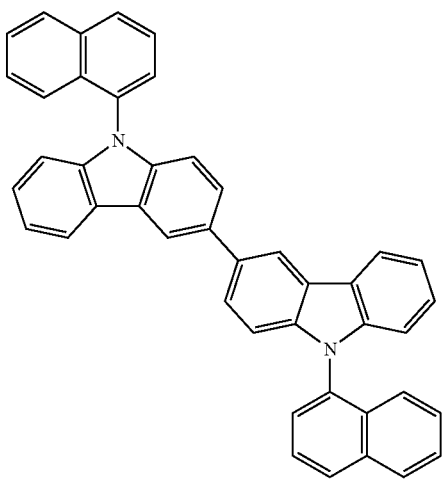
2-15
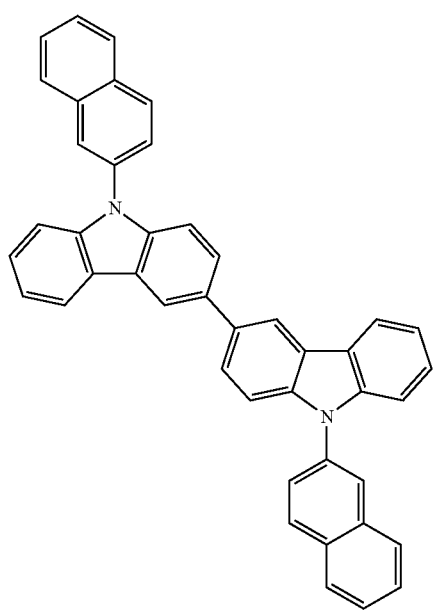
2-13
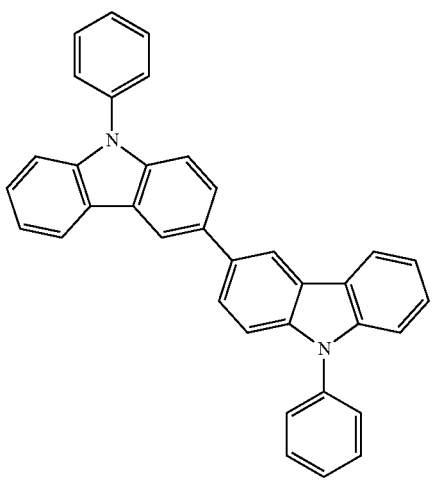
2-16

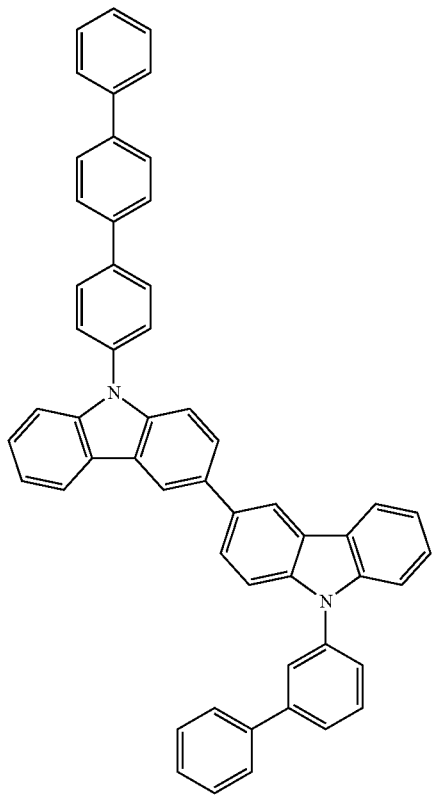
2-17
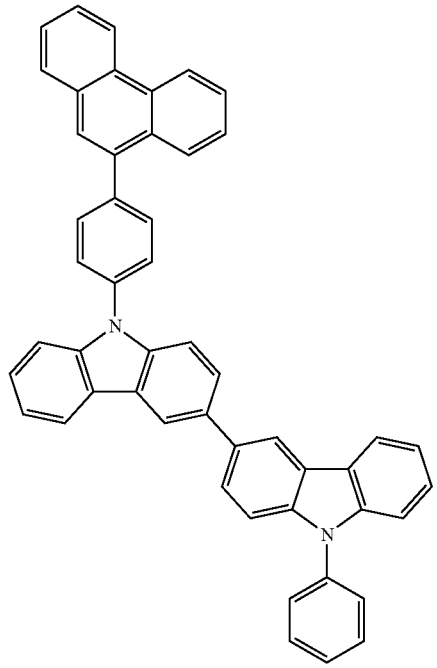
2-19
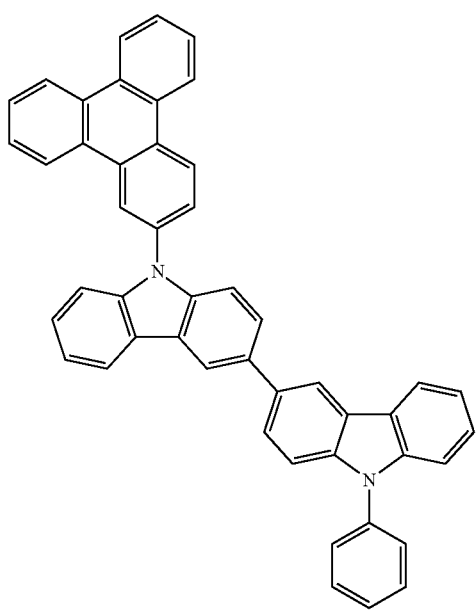
2-18
2-20
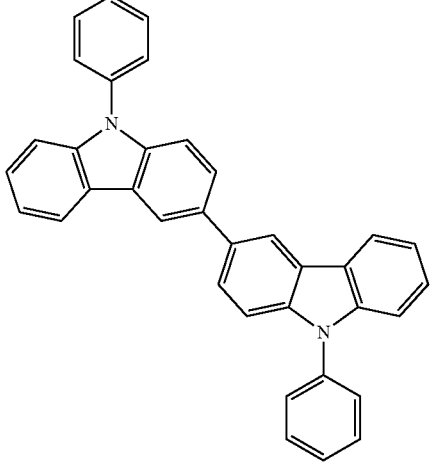

2-21
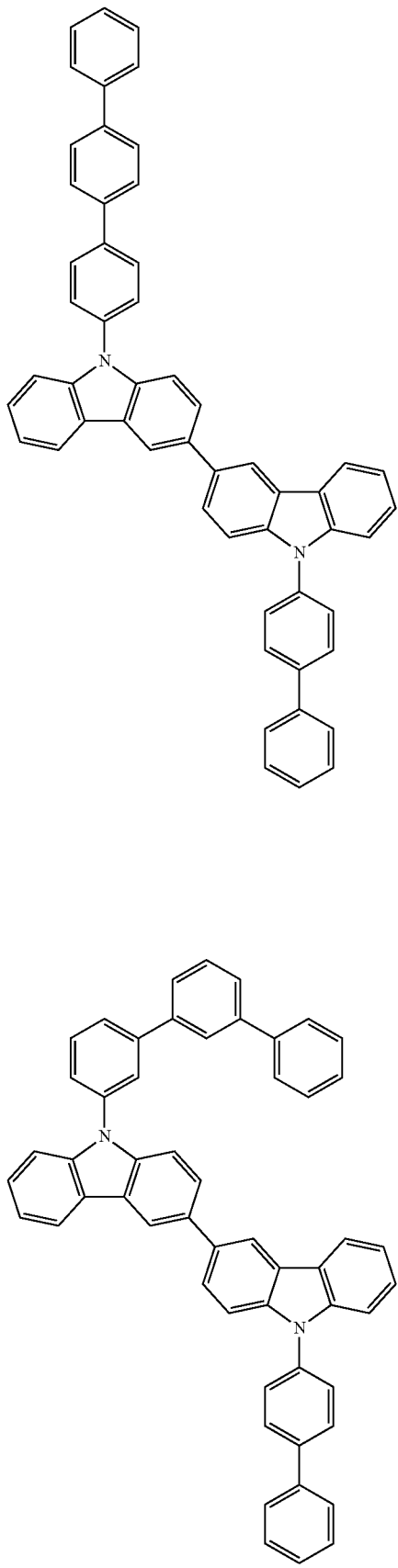
2-22
2-23
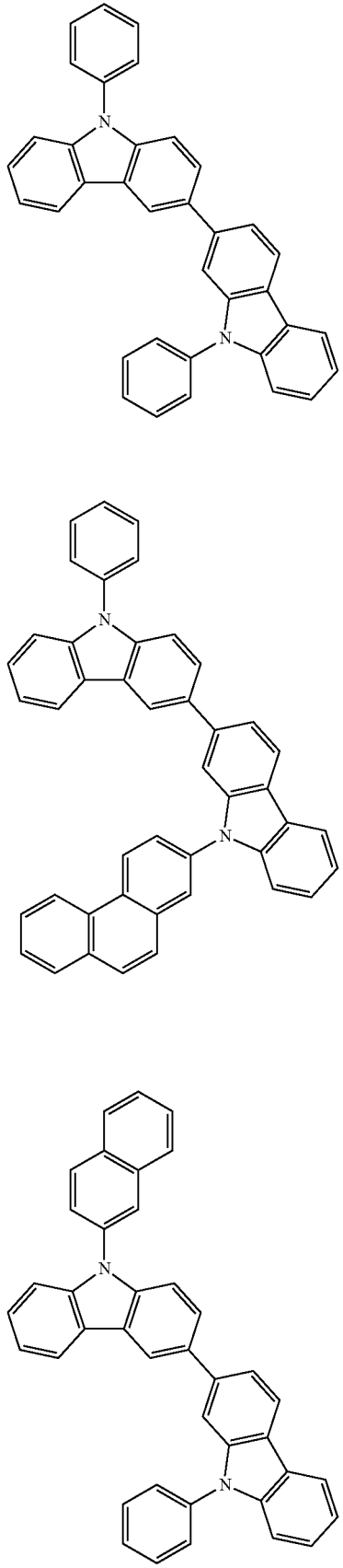
2-24
2-25

-continued
2-26
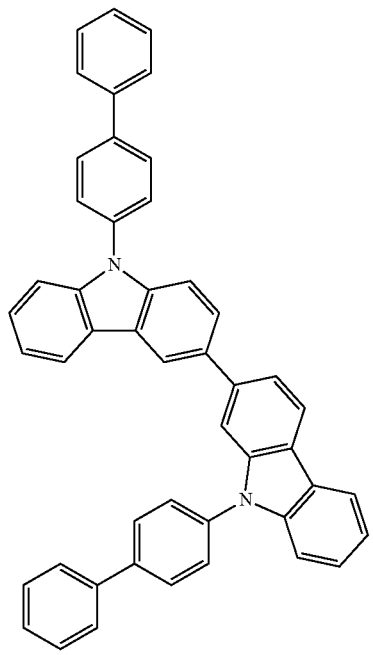
2-27
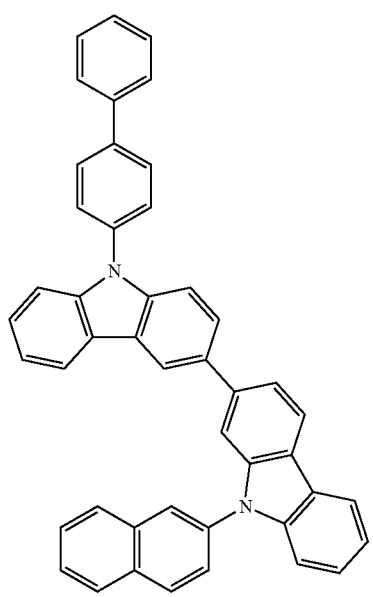
2-28
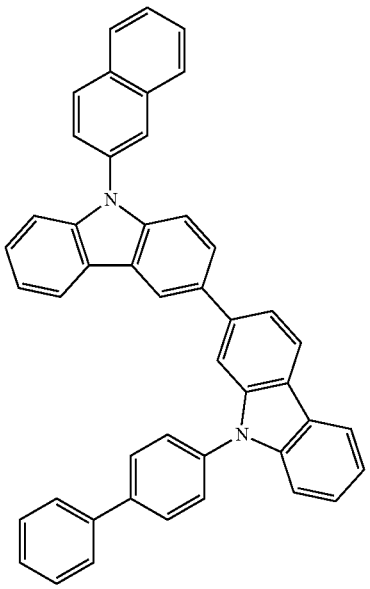
2-29
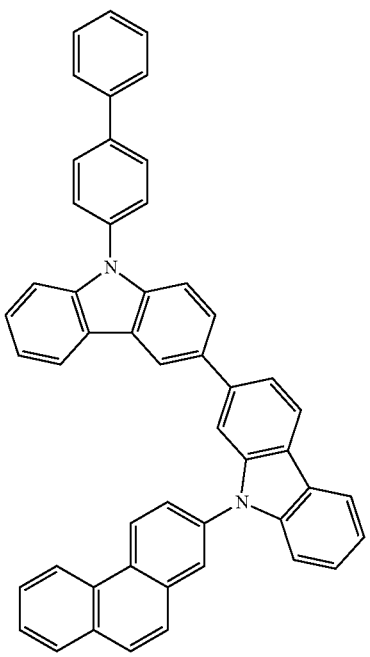

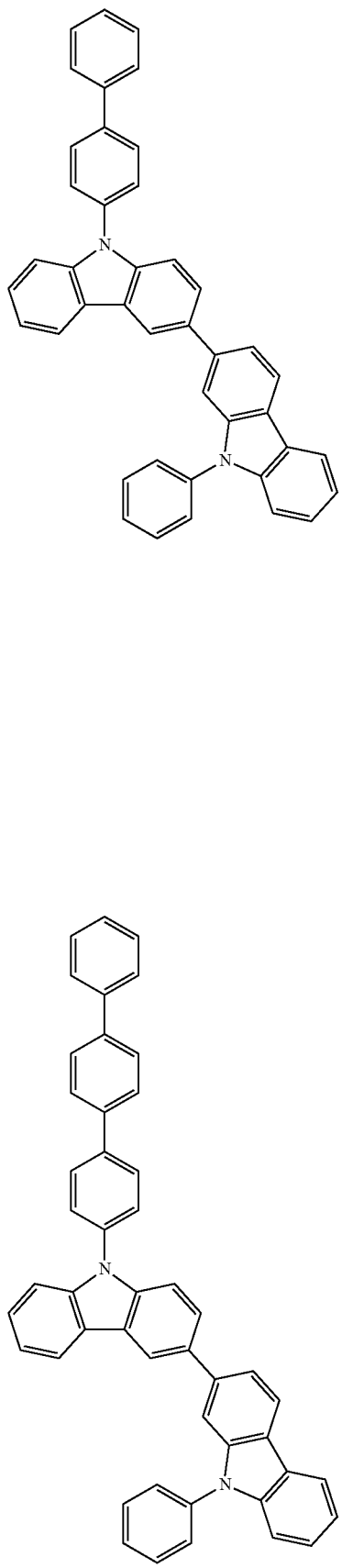

2-30

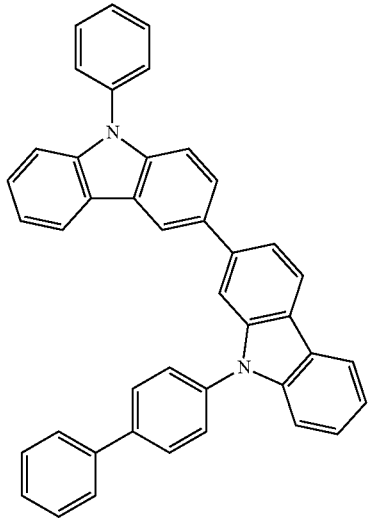

2-32

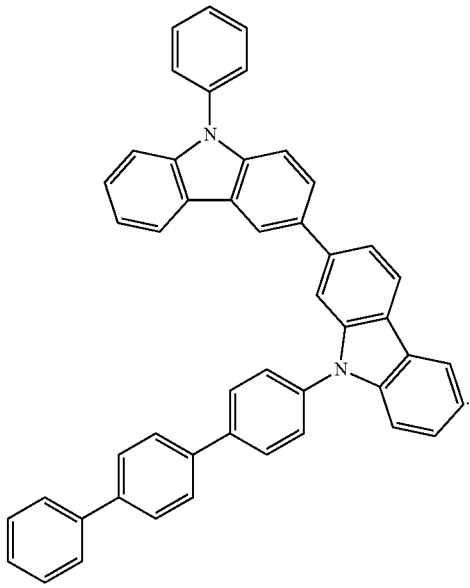

2-33

2-31

7. The organic light emitting device of claim 1, wherein the 2-2 host is a compound represented by Chemical Formula 3:

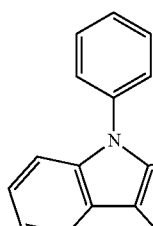

[Chemical Formula 3]

in Chemical Formula 3,
$L_4$ is a bond; a substituted or unsubstituted $C_{6-60}$ arylene; or a substituted or unsubstituted $C_{2-60}$ heteroarylene containing at least one of O, N, Si and S, $Ar_7$ and $Ar_8$ are each independently a substituted or unsubstituted $C_{6-60}$ aryl; or a substituted or unsubstituted $C_{2-60}$ heteroaryl containing at least one of O, N, Si and S, and Ar$_9$ is a substituted or unsubstituted C$_{2-60}$ heteroaryl containing at least one N.

8. The organic light emitting device of claim 7, wherein the compound represented by the Chemical Formula 3 is any one selected from the group consisting of:

3-1

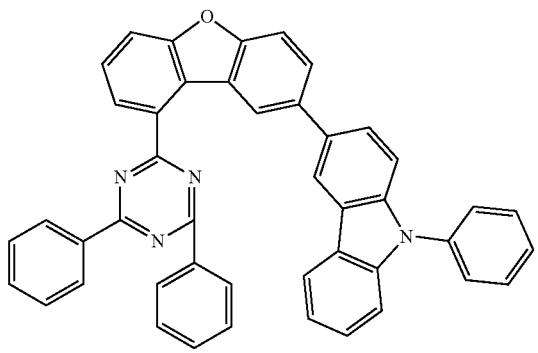

3-2

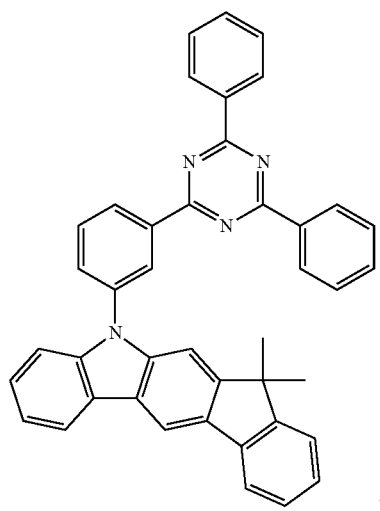

9. The organic light emitting device of claim 2, wherein the 3-2 host is a compound represented by Chemical Formula 3:

[Chemical Formula 3]

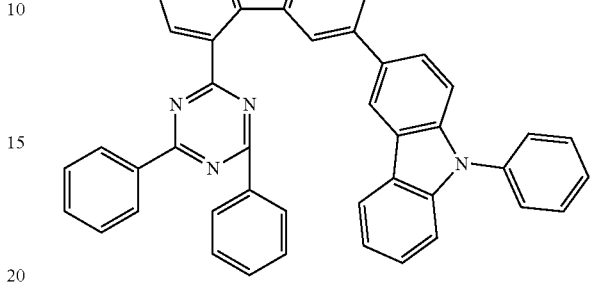

in Chemical Formula 3,

L$_4$ is a bond; a substituted or unsubstituted C$_{6-60}$ arylene; or a substituted or unsubstituted C$_2$-60 heteroarylene containing at least one of O, N, Si and S, Ar$_7$ and Ar$_8$ are each independently a substituted or unsubstituted C$_{6-60}$ aryl; or a substituted or unsubstituted C$_{2-60}$ heteroaryl containing at least one of O, N, Si and S, and Ar$_9$ is a substituted or unsubstituted C$_{2-60}$ heteroaryl containing at least one N.

10. The organic light emitting device of claim 9, wherein the compound represented by the Chemical Formula 3 is any one selected from the group consisting of:

3-1

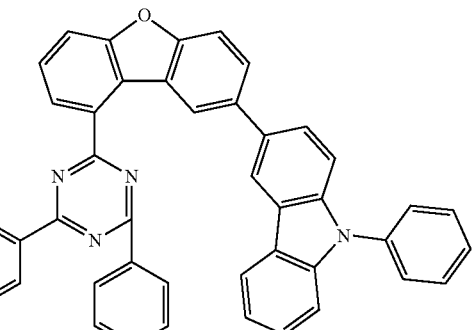

3-2

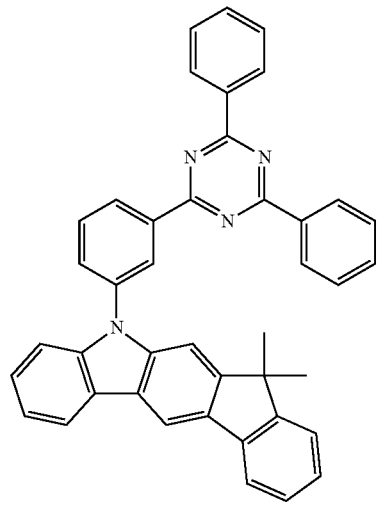

11. The organic light emitting device of claim 1, wherein the first light emitting layer further comprises a compound represented by Chemical Formula 4:

[Chemical Formula 4]

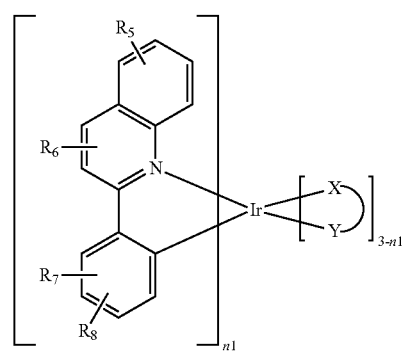

in Chemical Formula 4, n1 is 1 or 2,

R$_5$ to R$_8$ are each independently hydrogen; a substituted or unsubstituted C$_{1-60}$ alkyl; or a substituted or unsubstituted $C_{6-60}$ aryl; provided that one or more of $R_5$ to $R_8$ are a branched alkyl containing 4 or more carbons, and X—Y is an auxiliary ligand.

12. The organic light emitting device of claim 1, wherein the second light emitting layer further comprises a compound represented by Chemical Formula 5:

[Chemical Formula 5]

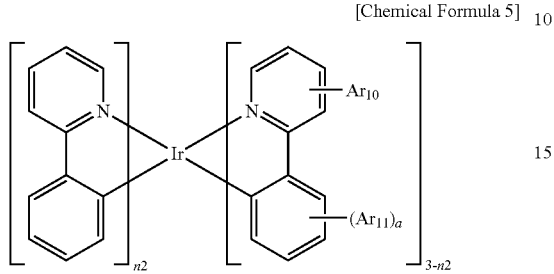

in Chemical Formula 5, n2 is 1 or 2, a is an integer of 0 to 4, and $Ar_{10}$ and $Ar_{11}$ are each independently a substituted or unsubstituted $C_{6-60}$ aryl; or a substituted or unsubstituted $C_{2-60}$ heteroaryl containing at least one of O, N, Si and S.

13. The organic light emitting device of claim 2, wherein the third light emitting layer further comprises a compound represented by Chemical Formula 6:

[Chemical Formula 6]

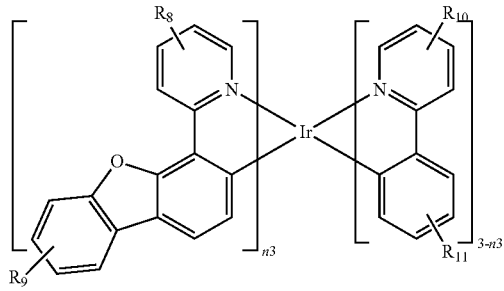

in Chemical Formula 6, n3 is 1 or 2, and $R_8$ to $R_{11}$ are each independently hydrogen; deuterium; halogen; nitrile; nitro; amino; a substituted or unsubstituted $C_1$-60 alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heterocyclic group containing at least one of O, N, Si and S.

* * * * *